(12) United States Patent
Hanaya et al.

(10) Patent No.: US 9,903,965 B2
(45) Date of Patent: Feb. 27, 2018

(54) SAMPLE MEASURING DEVICE

(71) Applicant: Hitachi, Ltd., Tokyo (JP)

(72) Inventors: Tomonori Hanaya, Tokyo (JP); Yujiro Akuta, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 4 days.

(21) Appl. No.: 15/028,157

(22) PCT Filed: Sep. 30, 2014

(86) PCT No.: PCT/JP2014/076174
§ 371 (c)(1),
(2) Date: Apr. 8, 2016

(87) PCT Pub. No.: WO2015/053134
PCT Pub. Date: Apr. 16, 2015

(65) Prior Publication Data
US 2016/0252634 A1    Sep. 1, 2016

(30) Foreign Application Priority Data

Oct. 9, 2013   (JP) ................................ 2013-211913
Oct. 9, 2013   (JP) ................................ 2013-211917

(51) Int. Cl.
*G01T 7/08*      (2006.01)
*G01N 35/04*     (2006.01)
*G01T 1/204*     (2006.01)

(52) U.S. Cl.
CPC .............. *G01T 7/08* (2013.01); *G01N 35/04* (2013.01); *G01T 1/204* (2013.01);
(Continued)

(58) Field of Classification Search
None
See application file for complete search history.

(56) References Cited

U.S. PATENT DOCUMENTS 3,553,454 A      1/1971   Olson et al.
3,654,472 A *    4/1972   Hof ..................... G21F 7/067
                                                          250/328
(Continued)

FOREIGN PATENT DOCUMENTS

FR   2277013 A1   1/1976
JP   50-99196     8/1975
(Continued)

OTHER PUBLICATIONS

Notice of Grounds for Rejection issued in the basic JP2013-211913 dated Dec. 16, 2014.
(Continued)

*Primary Examiner* — Jill A Warden
*Assistant Examiner* — Benjamin R Whatley

(57) ABSTRACT

Each adapter disposed on a rack includes a pair of arms that configure an opening/closing mechanism. During rack conveyance, a guiding block is slotted between a pair of legs contained in the rack. The opening/closing mechanism being abutted against the guiding block causes the opening/closing mechanism to perform an opening/closing operation. When the state of the opening/closing mechanism is changed from closed to open, a pre-measurement sample container is passed from a sample storage unit to a lifting mechanism. Subsequent to the post-measurement sample container being returned to the sample storage unit, the state of the opening/closing mechanism is changed from open to closed.

14 Claims, 35 Drawing Sheets

(52) U.S. Cl.
CPC .............. *G01N 2035/041* (2013.01); *G01N 2035/0405* (2013.01); *G01N 2035/0412* (2013.01)

(56) References Cited

U.S. PATENT DOCUMENTS

| | | | | |
|---|---|---|---|---|
| 3,663,816 | A | * | 5/1972 | Scherzer ............ G01T 7/08 250/364 |
| 3,722,719 | A | * | 3/1973 | Frank ............... G01T 7/08 250/328 |
| 4,001,585 | A | * | 1/1977 | Coutarel ............ B01L 9/06 198/345.3 |
| 4,029,961 | A | | 6/1977 | Lohr et al. |
| 4,040,533 | A | | 8/1977 | De Boer et al. |

FOREIGN PATENT DOCUMENTS

| | | | |
|---|---|---|---|
| JP | 51-111382 | A | 10/1976 |
| JP | 58-91163 | U | 6/1983 |
| JP | 9-264980 | A | 10/1997 |
| JP | 2007-176666 | A | 7/2007 |
| JP | 2007-278969 | A | 10/2007 |

OTHER PUBLICATIONS

Notice of Grounds for Rejection issued in the basic JP2013-211917 dated Jan. 6, 2015.
Extended European Search Report received for European Patent Application No. 14852443.2, dated May 8, 2017, 7 pages.

* cited by examiner

SAMPLE MEASURING DEVICE

TECHNICAL FIELD

The present invention relates to a sample measurement device, and in particular, to a sample measurement device which measures a radioactive substance in a sample using a liquid scintillator.

BACKGROUND ART

A sample measurement device is a device that individually measures a plurality of samples. Representative sample measurement devices include a liquid scintillation counter. The liquid scintillation counter has a rack-transporting mechanism which transports a rack holding a plurality of sample containers, a measurement unit which measures light caused by a radioactive substance contained in each sample container, a container transporting mechanism which transports the sample container between the rack and a measurement chamber unit, or the like. In the sample container, in addition to liquid sample, liquid scintillator is included. When a radiation (for example, a β ray) is emitted from the radioactive substance in the sample, light emission in the liquid scintillator is caused by the radiation. The light is detected by a pair of photomultiplier tubes forming the measurement unit.

In general, a shielding structure must be provided in order to block an extrinsic radiation at a periphery of a measurement chamber which stores the sample container to be measured. Such a shielding structure is formed from a metal which is very heavy. Therefore, it is more preferable that the shielding structure be placed below a rack placement surface rather than being placed above the rack placement surface. In addition, when a system is employed in which the sample container is transported upward from the rack, because a shaft which supports the sample container would exist within a lifting/lowering path during the measurement, there is a problem in that light shielding in the lifting/lowing path is difficult. Therefore, it is desired that the measurement chamber be provided below the rack placement surface, and also to withdraw the sample container downward from the rack.

Patent Document 1 discloses a liquid scintillation counter of the related art. In the liquid scintillation counter described therein, the measurement chamber is provided above a transport table for transporting the rack. Patent Document 2 discloses a rack transporting device which can be used for the liquid scintillation counter or the like.

CITATION LIST

Patent Literature
  [Patent Document 1] JP 2007-278969 A
  [Patent Document 2] JP 2007-176666 A

SUMMARY

Technical Problem

If a complex mechanism is provided in order to withdraw the sample container downward from the rack, a problem arises in that the cost is increased. While many drive sources are provided for the sample measurement device, it is desired to reduce the number of drive sources.

An advantage of the present invention is in the enablement of withdrawal of the sample container downward from the rack with a simple mechanism. Another advantage of the present invention is that the sample container can be held and released without the use of a dedicated drive source and a dedicated controller.

Solution to Problem (1) According to one aspect of the present invention, there is provided a sample measurement device, comprising: a rack that has a sample storage unit having an open/close mechanism; a rack-transporting mechanism that transports the rack on a transport surface; a guide block provided on the transport surface and that enters a lower part of the rack during transport of the rack to open or close the open/close mechanism; and a lifting/lowering mechanism that transports a sample container between the sample storage unit and a sample measurement chamber provided below the transport surface in an open state of the open/close mechanism.

According to the above-described configuration, the guide block enters the lower part of the rack by the transport of the rack, and the open/close mechanism provided on the sample storage unit is operated by the guide block. In an open state of the open/close mechanism, a sample container before measurement is sent from the sample storage unit to the lifting/lowering mechanism, and a sample container after the measurement is returned from the lifting/lowering mechanism to the sample storage unit. In the above-described configuration, because the sample measurement chamber is provided below the transport surface, it becomes unnecessary to place the shielding member, which is very heavy, at a high position. In addition, the light shielding of the lifting/lowering path for lifting/lowering the sample is also facilitated. Because the guide block causes the open/close mechanism to operate at a lower part of the rack, it is not necessary to provide a member which transmits an open/close drive force from an outer side of the rack to the inside of the rack.

According to another aspect of the present invention, preferably, in the sample measurement device, the open and close operations of the open/close mechanism is caused by a relative movement of the rack with respect to the guide block. According to such a configuration, a part of a rack-transporting force produced by the rack-transporting mechanism can be used to open the open/close mechanism. Therefore, it is not necessary to provide a dedicated drive source and a dedicated controller for an opening operation of the open/close mechanism. With such a configuration, the structure can be simplified. In order to close the open/close mechanism, it is desirable to use an elastic force accumulated by the opening operation of the open/close mechanism. Alternatively, a part of the rack-transporting force may be utilized for the closing operation.

According to another aspect of the present invention, preferably, in the sample measurement device, the guide block has: a front-side form that contacts the open/close mechanism during the relative movement to transition the open/close mechanism from a closed state to an open state; and a rear-side form that contacts the open/close mechanism during the relative movement to recover the open/close mechanism from the open state to the closed state; holding of the sample container is executed in the closed state; and holding of the sample container is released in the open state. According to such a configuration, the open/close mechanism is operated by the open/close mechanism contacting the guide block. An overall shape of the guide block is determined such that a desired opening operation and a desired closing operation are executed at desired timings. The front-side form is the form of a portion that first enters the lower part of the rack during the transport of the rack, and the rear-side form is a form on the side opposite the front-side form.

According to another aspect of the present invention, preferably, in the sample measurement device, the front-side form has a pair of front-side inclined surfaces that apply a press-spreading force on the open/close mechanism. According to such a configuration, when the open/close mechanism moves forward while contacting the pair of front-side inclined surfaces, the open/close mechanism is gradually changed from the closed state to the open state. The pair of front-side inclined surfaces have a function to convert a force in a longitudinal direction into a force on both sides in a short-side direction. By suitably setting the angle of the pair of the front-side inclined surfaces, it is possible to adjust an opening rate. Preferably, the pair of the front-side inclined surfaces has a line-symmetrical shape. Preferably, in the front-side form, a width in the short-side direction is gradually increased from a downstream side in the longitudinal direction to an upstream side.

According to another aspect of the present invention, preferably, in the sample measurement device, the rear-side form has a pair of rear-side inclined surfaces that allows a recovery movement of the open/close mechanism Specifically, when the open/close mechanism moves forward while contacting the pair of the rear-side inclined surfaces, the open/close mechanism is gradually changed from the open state to the closed state. In this case, it is preferable to provide, in order to maintain a contact state of the open/close mechanism with respect to the pair of inclined surfaces, a means that produces an elastic recovery force, in the open/close mechanism itself. In this case, the pair of the rear-side inclined surfaces has a function to restrict or adjust the rate of the closing operation to the short-side direction according to the position in the longitudinal direction. Preferably, the pair of the rear-side inclined surfaces has a line-symmetrical shape. Preferably, in the rear-side form, a width in the short-side direction is gradually decreased from a downstream side in the longitudinal direction toward an upstream side.

According to another aspect of the present invention, preferably, in the sample measurement device, the guide block has an intermediate form provided between the front-side form and the rear-side form that maintains the open state of the open/close mechanism, and the intermediate form has an opening that forms an upper end portion of a lifting/lowering path of the sample container. An open width of the open/close mechanism in the open state is set such that the sample container can be lowered into the opening and can be received from the opening. In the open state of the open/close mechanism, if the open/close mechanism protrudes in both outer sides from the lateral width of the rack (width in the short-side direction), it is preferable to provide a passage or the like in the rack to allow the protrusion.

According to another aspect of the present invention, preferably, in the sample measurement device, the guide block has: a front-side protrusion provided at a front side of the opening and that temporarily supports a lower surface of the sample container from below, after holding of the sample container by the open/close mechanism disappears; and a rear-side protrusion provided at a rear side of the opening that temporarily supports the lower surface of the sample container from below, until the holding of the sample container by the open/close mechanism is resumed. According to such a configuration, fall-off or unnecessary change in orientation of the sample container before the opening can be prevented, and fall-off or unnecessary change in orientation of the sample container at a position deeper than the opening can prevented. Preferably, a front edge portion (and a rear side portion) on the upper surface of each protrusion is formed as a tapered surface.

According to another aspect of the present invention, preferably, in the sample measurement device, the lifting/lowering mechanism has a head that has a placement surface on which the sample container is placed, and, in a state where the head is inserted into the opening, the placement surface is positioned at substantially the same height as an upper surface level of the front-side protrusion and the rear-side protrusion. The height and the form are preferably determined such that the protrusions and the head are not obstructed by the lower part of the sample container.

According to another aspect of the present invention, preferably, in the sample measurement device, the rack has a longitudinal direction and a short-side direction orthogonal to the longitudinal direction, the rack has a pair of legs distanced from each other in the short-side direction, and a width of the guide block in the short-side direction is substantially equal to a gap between the pair of the legs. According to such a configuration, when the guide block is inserted between the pair of the legs, the guide block restricts a change of orientation of the rack. In other words, the orientation and the position of the rack are determined According to another aspect of the present invention, preferably, in the sample measurement device, the guide block has a pair of tapered surfaces for centering in the short-side direction upon entrance to the pair of the legs. According to such a configuration, even when there is a deviation in a direction of travel of the rack, the orientation thereof can be forcefully changed to an appropriate orientation. With such a configuration, the operation of the open/close mechanism can be set appropriate, and it becomes easy to always position the sample container at an appropriate position.

According to another aspect of the present invention, preferably, in the sample measurement device, the rack has: a plurality of sample storage units arranged along a longitudinal direction; and a pair of legs distanced from each other in a short-side direction orthogonal to the longitudinal direction, each sample storage unit respectively has the open/close mechanism, and the guide block causes the plurality of open/close mechanisms to be sequentially opened and closed while passing a region between the pair of the legs during a transport process of the rack in the longitudinal direction. According to such a configuration, the open/close mechanisms are sequentially opened and closed at appropriate timings by the transport of the rack.

(2) According to another aspect of the present invention, there is provided a sample measurement device, comprising: a rack serving as a member that holds a plurality of sample containers arranged along a longitudinal direction and that has a pair of legs distanced from each other in a short-side direction orthogonal to the longitudinal direction; a transporting mechanism that transports, on a transport path extending in an X direction, the rack while coinciding the longitudinal direction with the X direction; a guide block which is a block provided on the transport path extending in the X direction, that enters between the pair of the legs, and that has a reference surface parallel to the X direction; and a pressing unit provided on one side of the guide block, that applies a pressing force on an outer surface of one leg to cause an inner surface of the one leg to closely contact the reference surface and form a state of an appropriate position and an appropriate orientation of the rack.

According to the above-described configuration, when the pressing unit applies the pressing force on the outer surface of one leg, the inner surface of the one leg closely contacts the reference surface. Because the reference surface is a surface parallel to the X direction, with the close contact, the longitudinal direction of the rack can be precisely adapted to the X direction. In addition, in the state where the inner surface of one leg is in close contact with the reference surface, the rack position in the Y direction is also naturally set appropriate. In other words, with the above-described configuration, the position and the orientation of the rack can be easily set appropriate basically by simply adjusting the position and the orientation of the guide block.

According to another aspect of the present invention, preferably, in the sample measurement device, the guide block is placed at a location for introducing or taking out a sample container to be measured, and the sample container to be measured is introduced or taken out in a state where the position and the orientation of the rack are set appropriate.

According to another aspect of the present invention, preferably, in the sample measurement device, the sample container to be measured is positioned at a reference position in the X direction, the reference surface is a surface spreading in an upstream side and a downstream side in the X direction from the reference position in the X direction, and the pressing unit includes a first contact member that applies a first pressing force on the outer surface of the one leg in an upstream side in the X direction relative to the reference position in the X direction, and a second contact member that applies a second pressing force on the outer surface of the one leg at a downstream side in the X direction relative to the reference position in the X direction. According to such a configuration, pressing forces may be produced on the rack in front and rear of the reference position in the X direction, to reliably cause the inner surface of the one leg to closely contact the reference surface. The first contact member and the second contact member may be configured to continuously contact the rack or intermittently contact the rack. In the former case, the contact members are preferably configured to reduce a sliding resistance caused in the movement of the rack in the X direction. In the latter case, it is preferable to provide a mechanism that moves the two contact members forward when the rack is stopped.

According to another aspect of the present invention, preferably, in the sample measurement device, the first contact member is a first roller, and the second contact member is a second roller. According to such a configuration, it is possible to set the sliding resistance during the movement of the rack in the X direction very low while forming the close contact state. The reference surface is preferably a completely flat surface parallel to the X direction. Preferably, a tapered surface is formed on the front end side and the rear end side thereof.

According to another aspect of the present invention, preferably, in the sample measurement device, the pressing unit comprises a first movable member having a first front-end section rotatably holding the first roller and a first rear-end section at a side opposite the first front-end section, a second movable member having a second front-end section rotatably holding the second roller and a second rear-end section on a side opposite the second front-end section, and an elastic member that applies an elastic force on the first movable member and the second movable member.

According to another aspect of the present invention, preferably, in the sample measurement device, the pressing unit has a common rotational axis forming a rotational axis of the first movable member and a rotational axis of the second movable member, and the elastic member is provided between the first rear-end section and the second rear-end section. According to such a configuration, an elastic force produced by a single elastic member is transmitted to two rollers through two movable members. With such a configuration, the mechanism can be simplified. In addition, with such a configuration, it is easy to set the pressing forces by two rollers equal to each other.

According to another aspect of the present invention, preferably, in the sample measurement device, a center of rotation of the first roller and a center of rotation of the second roller are set at a position farther away from the guide block relative to the common rotational axis in a Y direction orthogonal to the X direction. According to such a configuration, resistance when the front-end section of the one leg is received between the first roller and the reference surface can be reduced. In preparation of the case of return-transporting the rack and in order to produce equal pressing forces, it is preferable to set a negative offset also for the center of rotation of the second roller.

According to another aspect of the present invention, preferably, in the sample measurement device, a lifting/lowering path for lifting/lowering the sample to be measured is provided between the rack and a sample measurement chamber, and the guide block has an opening forming an upper end of the lifting/lowering path. According to such a configuration, the lifting/lowering path and the guide block can be practically physically integrated with each other, thereby facilitating appropriate positioning of the rack with respect to the lifting/lowering path. According to such a positioning of the rack, an advantage can be obtained of reducing influences on the transport surface by a machining error, an assembly error, or the like of a wall member, a separating member, or the like.

DESCRIPTION OF EMBODIMENTS

Preferred embodiments of the present invention will now be described with reference to the drawings.

Figure 1:
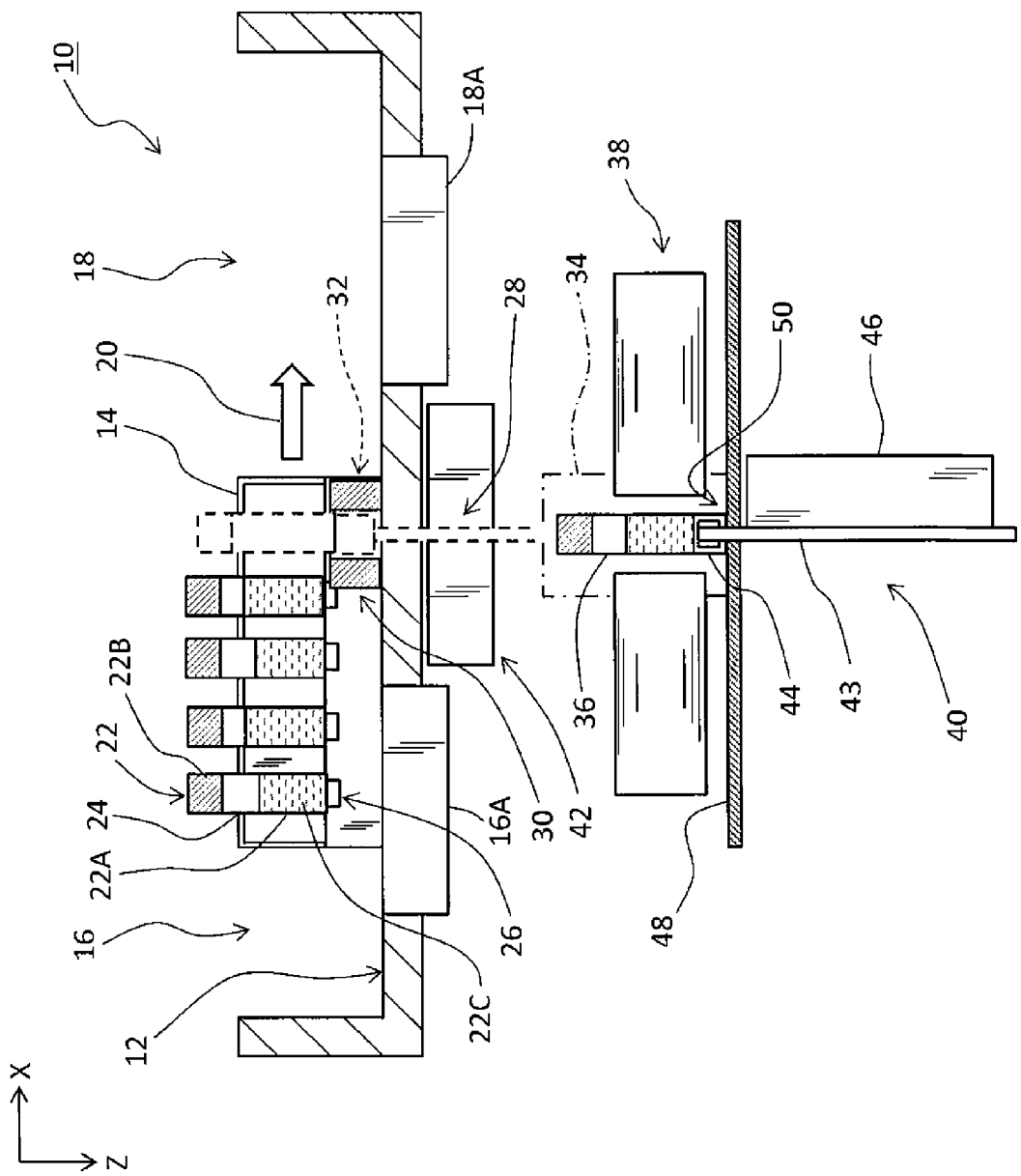
FIG. 1 is a diagram showing an overview of a sample measurement device according to a preferred embodiment of the present invention.
Figure 2:
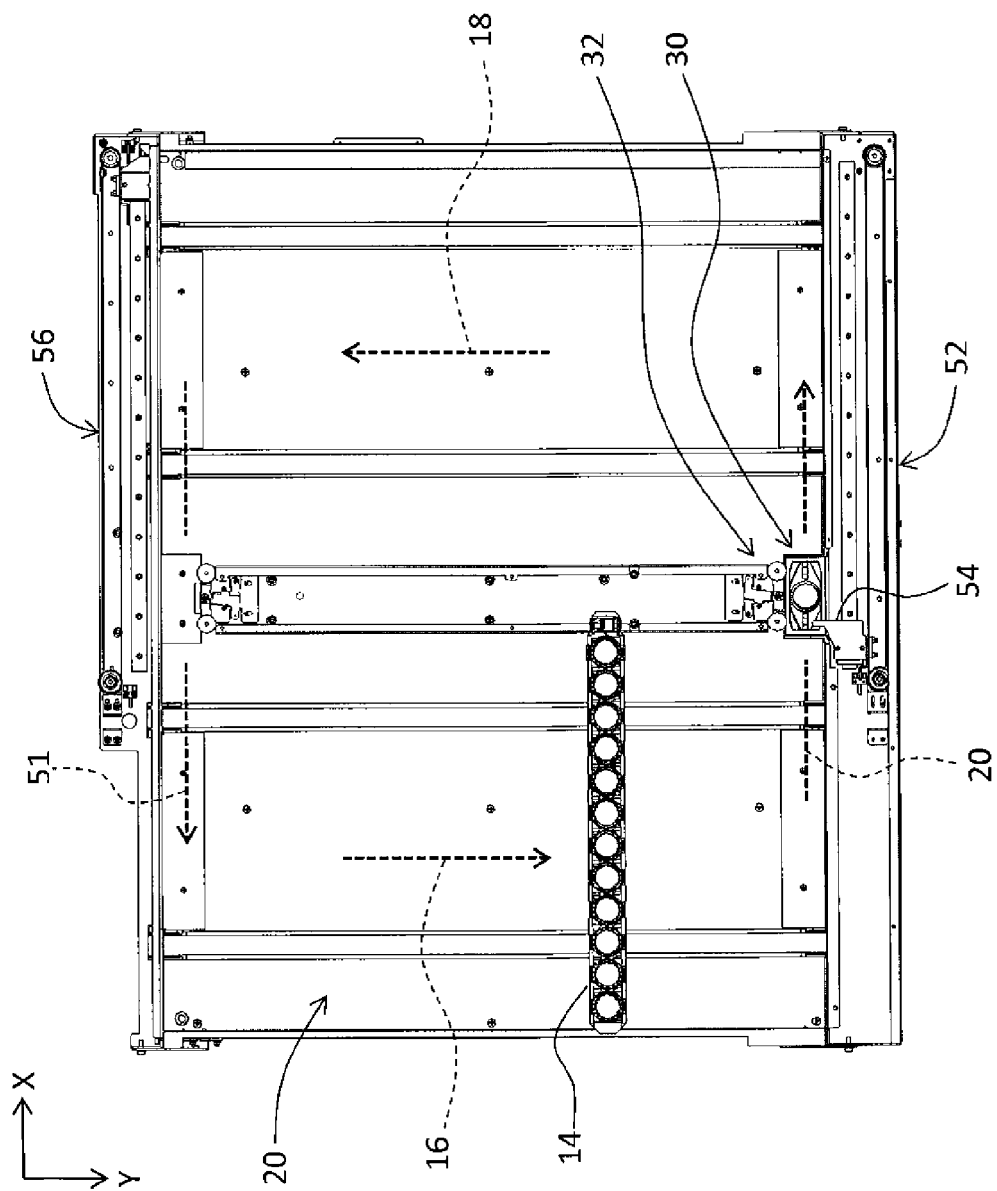
FIG. 2 is a top view of a sample measurement device.
Figure 3:
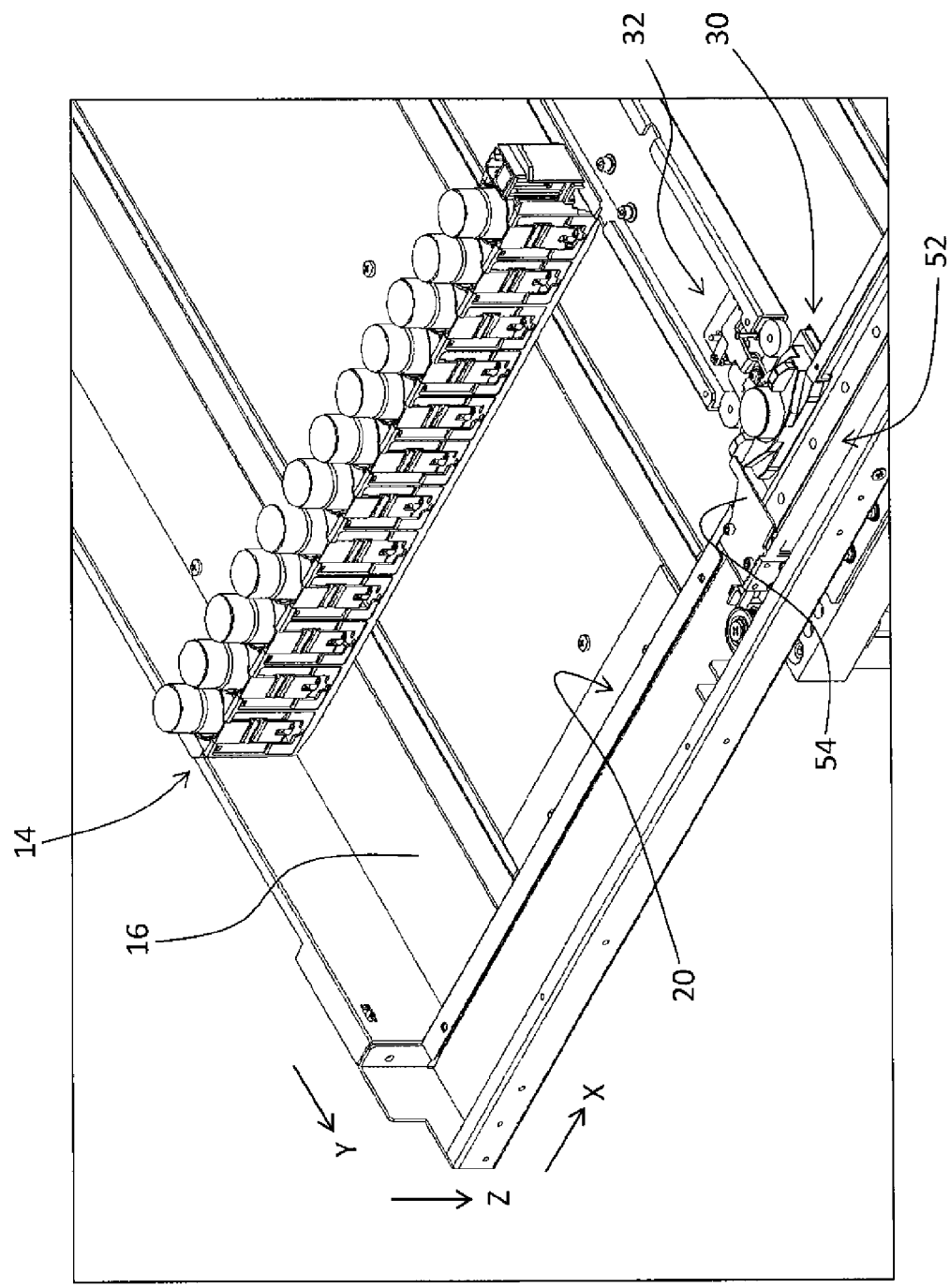
FIG. 3 is a perspective view of a sample measurement device.

(A) Overview of Sample Measurement Device (FIGS. 1-3)

FIG. 1 shows a sample measurement device according to a preferred embodiment of the present invention. In the present embodiment, the sample measurement device shown in FIG. 1 is a scintillation counter. The scintillation counter measures a radioactive substance contained in a sample using a liquid scintillator. Alternatively, the present invention can be applied to other sample measurement devices.

FIG. 1 is a schematic diagram showing an overall structure of a sample measurement device 10. An X direction is a first horizontal direction, a Y direction is a second horizontal direction, and a Z direction is a vertical direction. The sample measurement device 10 has a transport table 12 having a transport surface extending in the X direction and the Y direction. A plurality of racks 14 are transported on the transport table 12. In the present embodiment, a Y transport path 16, an X transport path 20, a Y transport path 18, and another X transport path are provided on the transport table 12. A transporting mechanism 16A is a mechanism for transporting the rack 14 in a forward direction in the Y direction on the Y transport path 16. A transporting mechanism 18A is a mechanism for transporting the rack 14 in a reverse direction in the Y direction on the Y transport path 18. A mechanism for transporting the rack 14 in the forward direction in the X direction on the X transport path 20 is not shown in FIG. 1. Similarly, a mechanism for transporting the rack 14 in the reverse direction in the X direction on the other X transport path is not shown in FIG. 1.

The rack 14 has a longitudinal direction and a short-side direction. The longitudinal direction is a direction of arrangement of a plurality of storage units 24. The short-side direction is a direction orthogonal to the longitudinal direction. In each storage section or part 24, a sample container 22 is held. The sample container 22 is, for example, a vial, a test tube, or the like. The sample container 22 includes a body 22A and a cap 22B. In the body 22A, a liquid sample 22C is stored. In the body 22A, a liquid scintillator for measuring the radioactive substance in the liquid sample is also stored. In general, the liquid scintillator is a substance that emits light upon reception of a radioactive ray ($\beta$ ray in the present embodiment).

In the present embodiment, as will be described later in detail, an adaptor is mounted for each storage unit 24 on the rack body. As a function of the adapter, an open/close mechanism 26 is realized. That is, the rack 14 has a plurality of open/close mechanisms 26 corresponding to the plurality of storage units 24. Each open/close mechanism 26 takes a closed state and an open state. In the closed state, the open/close mechanism 26 holds the sample container 22, and in the open state, the holding of the sample container 22 is released and the sample container 22 is freed. In the present embodiment, the sample container 22 which is set as the measurement target is withdrawn downward from the rack 14.

A guide block 30 is fixedly placed at a location where a target container is introduced or extracted on the X transport path 20 on the transport table 12. The guide block 30 is a member that enters a lower part of the rack 14. More specifically, the guide block 30 is a member that enters between a pair of legs of the rack 14, to apply an opening force on each open/close mechanism 26. In addition, the guide block 30 is a member that cooperates with a pressing unit 32 to be described later, to achieve an appropriate position and an appropriate orientation of the rack. The guide block 30 has an opening in its center, penetrating in the vertical direction. The opening corresponds to an upper end of a lifting/lowering path 28. The lifting/lowering path 28 is a passage for the sample container which is set as the measurement target to be lifted or lowered between the rack 14 and a sample measurement chamber 34. In the present embodiment, the guide block 30 is positioned with high precision with respect to the lifting/lowering path 28. In other words, as will be described later, the guide block 30 is physically integrated to a structure that forms the lifting/lowering path 28.

In the present embodiment, the pressing unit 32 is provided in order to achieve an appropriate position and an appropriate orientation of the rack 14 during the introduction or extraction of an individual sample container. The pressing unit 32 applies a pressing force on an outer surface of one leg of a pair of legs of the rack 14, to thereby cause an inner surface of the one leg to closely contact a reference surface of the guide block 30. With the formation of such a close contact state, the position and orientation of the rack 14 can be set appropriate.

During the sample measurement, a sample container 36 which is set as the measurement target is stored in the sample measurement chamber 34. A lifting/lowering mechanism 40 is provided for lifting and lowering the sample container 36.

With the lifting/lowering mechanism 40, the sample container 36 can be moved in the up-and-down direction in the lifting/lowering path 28.

In the present embodiment, the lifting/lowering mechanism 40 has a shaft 43, a head 44 provided at an upper end of the shaft 43, a slide mechanism 46 which drives the shaft 43, or the like. As will be described later, in the handing of the sample container between the rack 14 and the head 44, the head 44 is inserted into an opening formed in the guide block 30. In this state, the open/close mechanism 26 provided on the storage unit 24 positioned immediately above the opening is set in the open state. More specifically, in the transport process of the rack 14, the open/close mechanism 26 contacts the guide block 30, and the open/close mechanism 26 receives an opening force in the horizontal direction from the guide block 30 so that the open state of the open/close mechanism 26 is formed.

The sample measurement chamber 34 is mounted on a base 48. When light emission is caused in the sample container 36 stored in the sample measurement chamber 34, the light is detected by a pair of photomultiplier tubes 38. The pair of photomultiplier tubes 38 are provided for executing a coincidence counting process. In the present embodiment, a special light-shielding structure 50 is provided at a lower part of the sample measurement chamber 34. With the light-shielding structure 50, intrusion of extrinsic light through the surface of the shaft 43 into the sample measurement chamber 34 is prevented. The light-shielding structure 50 is provided over a lower surface of the head 44 and an upper surface of the base 48 to which the lower surface of the head 44 contacts. In the head 44 also, a predetermined light-shielding structure is provided. These elements will be described later in detail.

In the present embodiment, the sample measurement chamber 34 is provided below the transport table 12. Therefore, an advantage can be obtained in that a very heavy shielding member provided at the periphery of the sample measurement chamber 34 can be placed at a lower side of the transport table 12. In addition, as will be described below, during the sample measurement, when extrinsic radiation is blocked and extrinsic light is blocked at a predetermined location on the lifting/lowering path 28, because there is no shaft 43 in this location, the extrinsic radiation and extrinsic light can be easily and reliably blocked.

Specifically, a shutter mechanism 42 is provided on the lifting/lowering path 28, in a manner to extend across the path. The shutter mechanism 42 in the present embodiment includes an upper shutter mechanism and a lower shutter mechanism. That is, a double shutter mechanism is realized. The upper shutter mechanism is a mechanism which inserts a radiation-shielding member at an upper side of the sample measurement chamber 34 to block the extrinsic radiation, and the lower shutter mechanism is a mechanism which inserts a light-shielding plate across the lifting/lowering path 28 to block intrusion of extrinsic light from above.

In the sample measurement device 10 of the present embodiment, the rack 14 is intermittently sent in the X direction on the X transport path 20 and in an orientation where the longitudinal direction is coincided with the X direction. In this case, the guide block 30 enters a lower part of the rack 14, and the open/close mechanisms 26 provided on the storage units 24 are sequentially activated. The rack 14 stops in a state where a center line of each storage unit 24 and a center line of the lifting/lowering path 28 are matched. In this state, a sample container before measurement is sent from the rack 14 into the sample measurement chamber 34. After the measurement is completed, the sample container 36 after measurement is returned to the original sample container storage unit. Then, with the transport of the rack 14, the open/close mechanism 26 is returned from the open state to the closed state in the storage unit 24 receiving the sample container. This sequence of processes is repeatedly executed for each storage unit 24.

FIG. 2 is a top view of the sample measurement device shown in FIG. 1. As already described, on the transport table 12, the rack 14 is transported in the horizontal direction. As the transport path of the rack 14, in the present embodiment, the Y transport path 16, the X transport path 20, the Y transport path 18, and the X transport path 51 are provided. Normally, many racks 14 are placed on the transport table 12, and each rack 14 is sequentially transported on each transport path.

A center position on the X transport path 20 is a reference position for introducing and extracting the sample container. The guide block 30 is provided in a manner such that a center of the guide block 30 matches the reference position. Near the guide block 30, the pressing unit 32 which realizes a pressing function to the rack 14 is provided. On the X transport path 20, the rack 14 is transported in the X direction by the transporting mechanism 52 in a manner such that the longitudinal direction of the rack 14 is parallel to the X direction. The transporting mechanism 52 has a hook member 54. As will be described later, while a tip of the hook member 54 is hooked with respect to the protruding portion of the rack 14, the hook member 54 is moved in the X direction. With this process, the rack 14 is transported in the X direction. The hook member 54 is configured so as not to obstruct operations of the open/close mechanisms even in a state where the tip portion thereof is engaged with respect to the rack 14.

In the X transport path 50 at the opposite side also, a transporting mechanism 56 for transporting the rack 14 in the X direction is provided. The transporting mechanism 56 basically has the same structure as the transporting mechanism 52. On the X transport path 50, no member corresponding to the guide block 30 is provided, but a pressing unit having the same structure as the pressing unit 32 is placed.

FIG. 3 is a perspective view showing a part of the transport table. As described above, on the Y transport path 16, the rack 14 is transported in the Y direction. In this case, the rack 14 is translated in a manner such that the short-side direction of the rack 14 is directed to the Y direction. On the X transport path 20, the rack 14 is transported in a manner such that the longitudinal direction of the rack 14 is directed to the X direction. In order to strictly match the longitudinal direction of the rack 14 with the X direction during introduction and extraction of the sample container, the pressing unit 32 described above presses one leg of the rack 14 toward the side of the guide block 30.

The guide block 30 is provided on the reference position on the X transport path 20. In FIG. 3, a head which is a part of the lifting/lowering mechanism is entered in the opening of the guide block 30. That is, in FIG. 3, the head is in a lifted state. As described above, the transporting mechanism 52 has the hook member 54.

(B) Rack and Adapter (FIGS. 4-17)

Next, the rack and the adapter will be described in detail.

Figure 4:
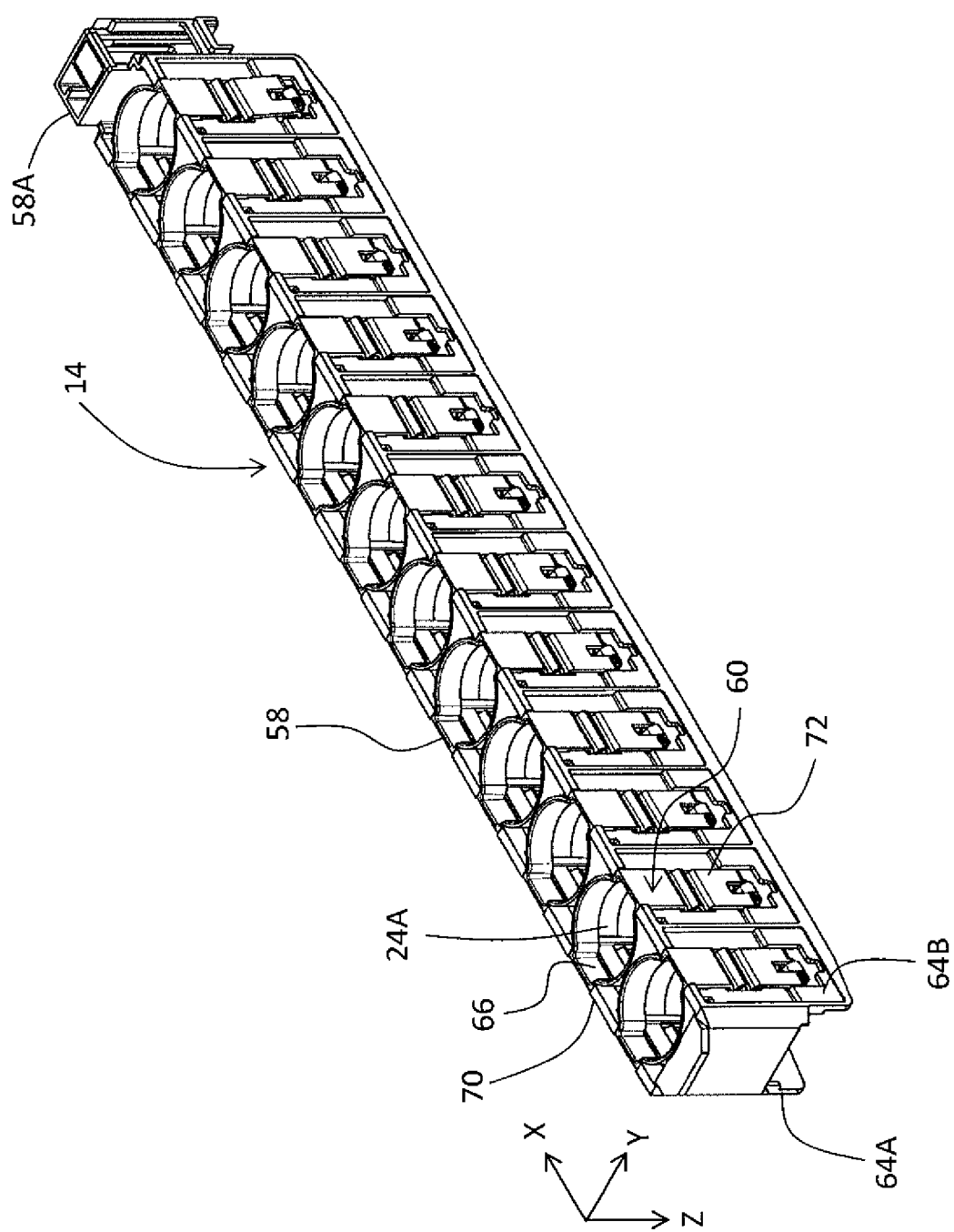
FIG. 4 is a first perspective view of a rack.

FIG. 4 is a perspective view showing the rack 14 viewed from diagonally above. The rack 14 holds a plurality of sample containers arranged in the longitudinal direction (X direction in FIG. 4). The rack 14 includes a rack body 58, and a plurality of adapters 60 detachably attached to the rack body 58. A plurality of storage units 24 are provided in the rack 14, and the adapter 60 is provided for each storage unit 24. As will be described later in detail, the adapter 60 includes a ring-shaped frame 66, and a pair of arms 70 and 72 extending from the ring-shaped frame 66 in the downward direction. The arm 70 and the arm 72 as a whole form the open/close mechanism described above.

The rack 14 has a pair of legs 64A and 64B distanced from each other in the short-side direction. Each of the legs 64A and 64B extends in the longitudinal direction. A region between the pair of legs 64A and 64B forms a cavity section for allowing the guide block to pass. A front side and a rear side of the cavity section are both openings. On a front end of the rack 14, a protrusion portion 58A is provided. The tip of the hook member is inserted into the rack opening of the protrusion portion 58A. Alternatively, a rack may be used in which, in addition to the longitudinal direction, a plurality of storage units are arranged in the short-side direction.

Figure 5:
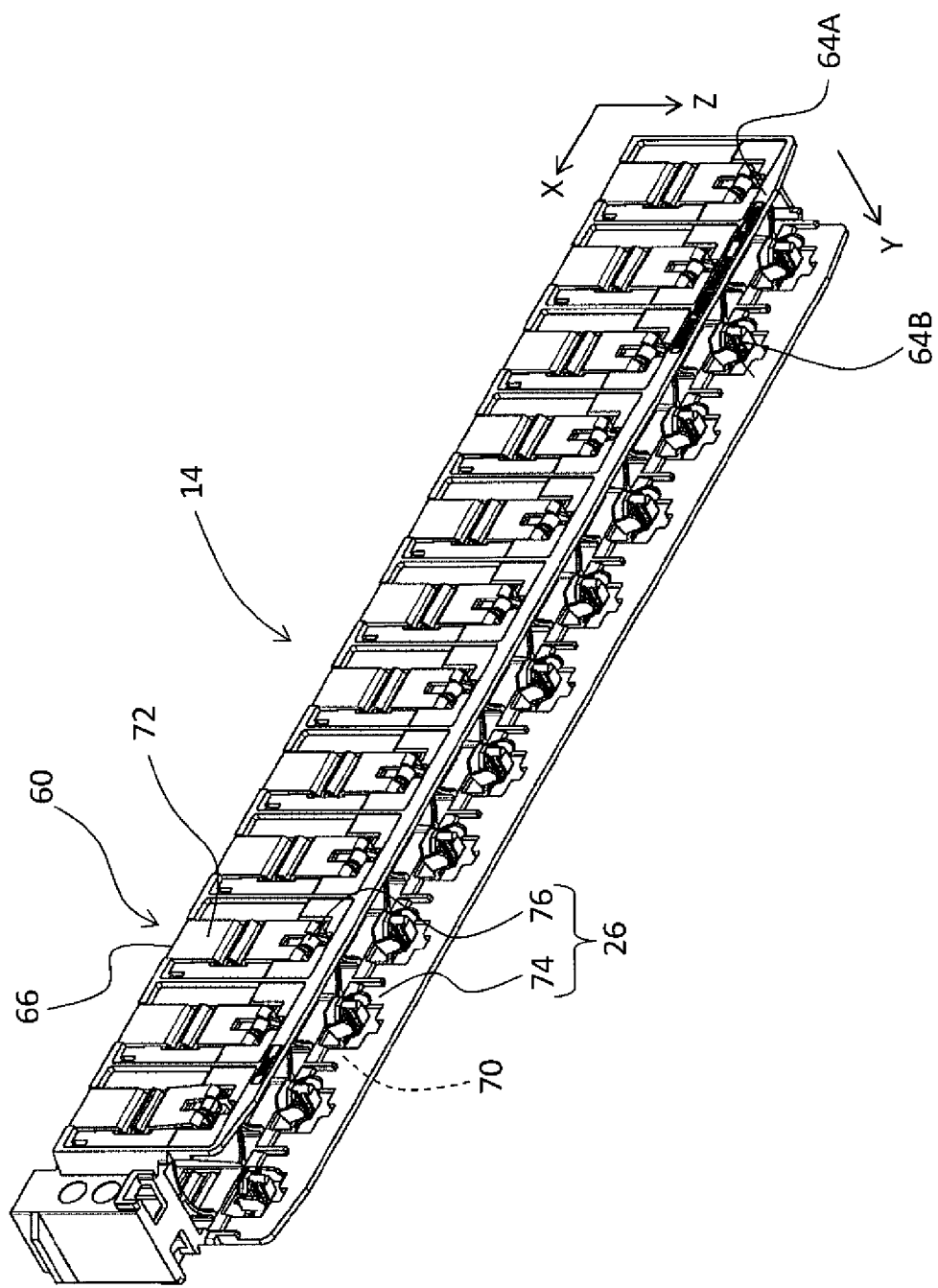
FIG. 5 is a second perspective view of a rack.

FIG. 5 is a perspective view of the rack 14, viewed from diagonally below. As described above, the rack body has the pair of legs 64A and 64B. The adapter 60 has the ring-shaped frame 66 and the pair of arms 70 and 72 placed in a distanced manner from each other in the short-side direction. The pair of arms 70 and 72 have a pair of lower end structures 74 and 76, which form a primary portion of the open/close mechanism 26.

Figure 6:
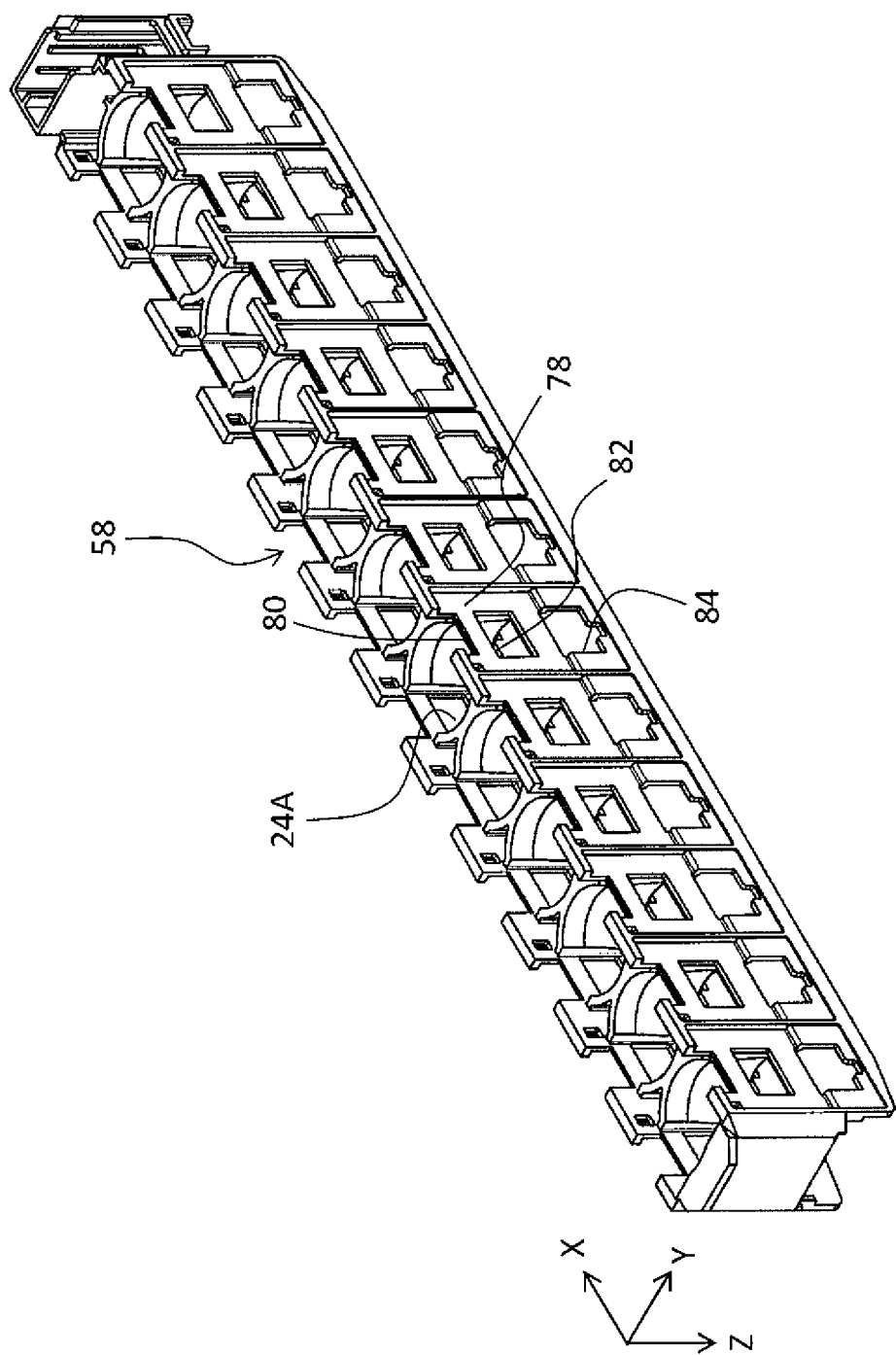
FIG. 6 is a first perspective view of a rack body.
Figure 7:
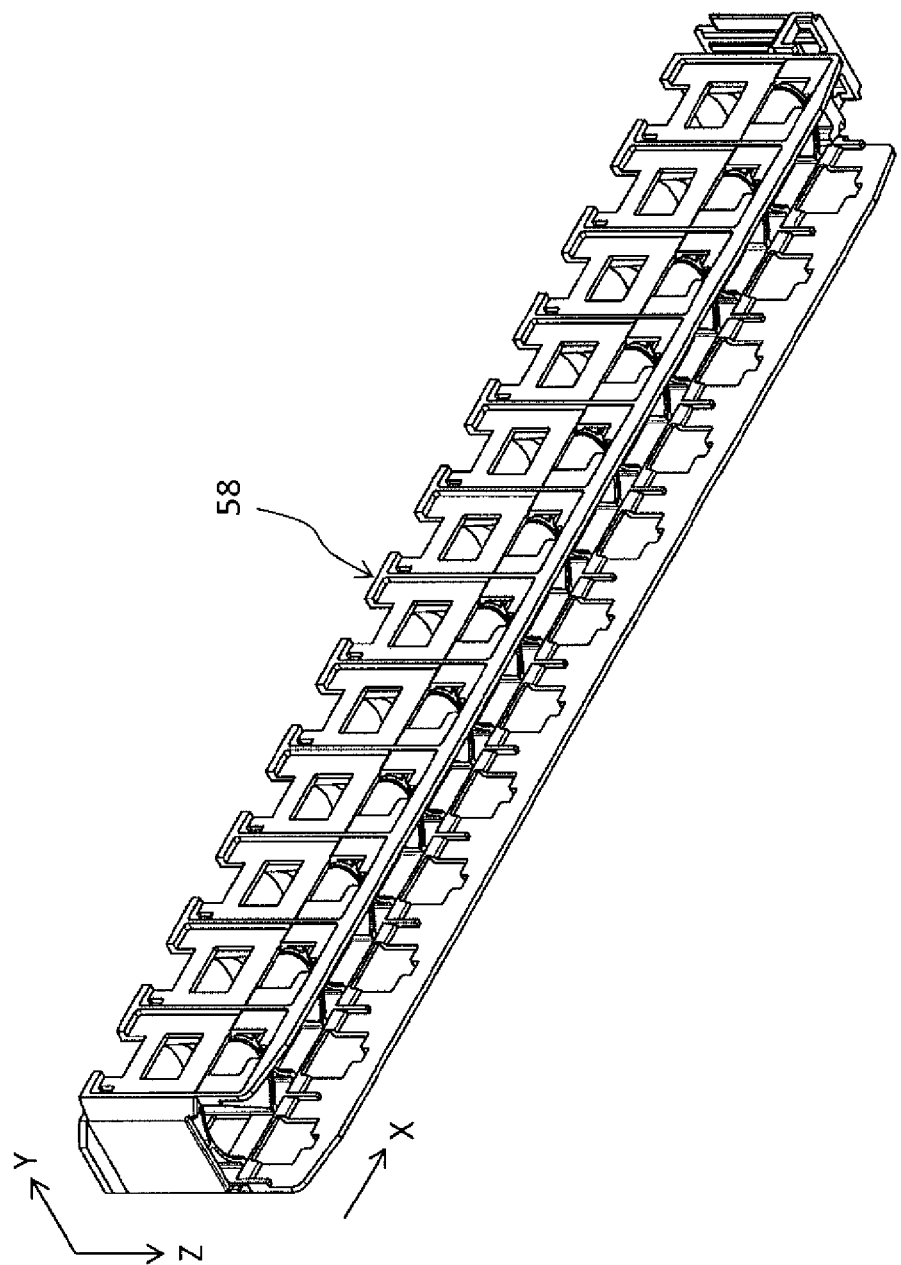
FIG. 7 is a second perspective view of a rack body.

FIG. 6 shows the rack body 58 viewed from diagonally above. The rack body 58 has a plurality of storage holes 24A arranged in the longitudinal direction. In each storage hole 24A, a one-side surface structure and an other-side surface structure are provided on both sides in the short-side direction. Because these structures have a symmetric shape, the one-side surface structure will be described as a representative of these two structures. A side plate 78 extending in the vertical direction is provided on one side of the storage hole 24A. A rib formed as a thick portion is provided between two adjacent side plates 78 or over the two adjacent side plates 78. A substantial portion of the side plate 78 is formed as a thin portion. At an upper part of the side plate 78, an upper opening 82 is provided, and, at a lower part of the side plate 78, a lower opening 84 is formed. The upper opening 82 and the lower opening 84 are each an opening penetrating in the short-side direction. FIG. 7 shows the rack body 58 viewed from diagonally below.

Next, a structure and a function of the adapter will be described with reference to FIGS. 8-17.

Figure 8:
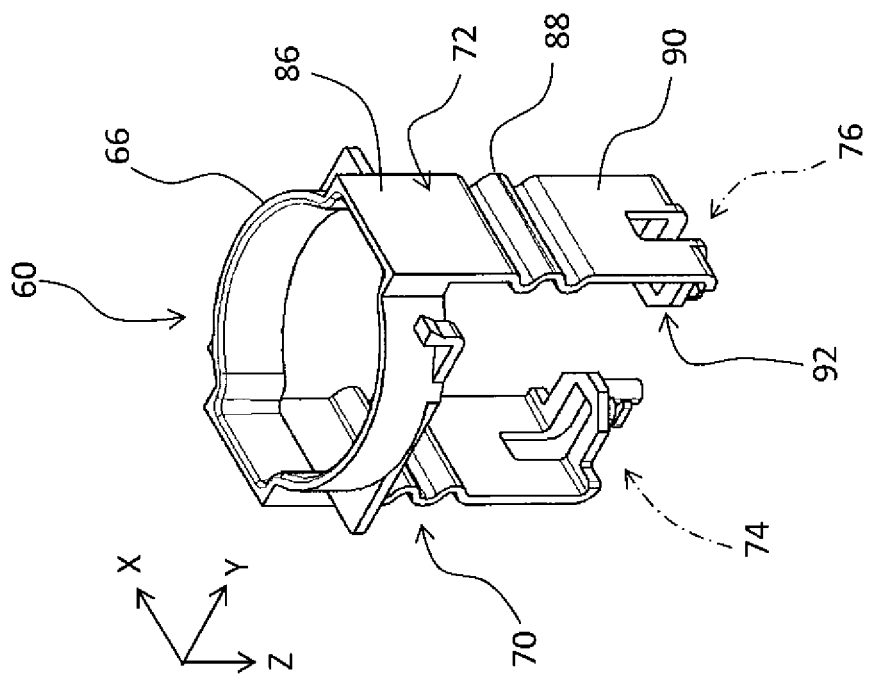
FIG. 8 is a first perspective view of an adapter.

FIG. 8 shows the adapter 60 viewed from diagonally above. As described above, the adapter 60 has the ring-shaped frame 66 and the pair of arms 70 and 72 extending from the ring-shaped frame 66 in the downward direction. The ring-shaped frame 66 has a ring shape corresponding to the storage hole, and has a rib or the like. The pair of arms 70 and 72 are distanced from each other in the short-side direction (Y direction in FIG. 8), and the sample container is maintained between the arms. The arm 70 and the arm 72 have a form symmetric with each other. Here, the arm 72 will be described. The arm 72 has an upper portion 86 connected to the ring-shaped frame 66, a wave-shaped portion 88 serving as a bending portion provided at a lower side of the upper end portion 86, and a lower end portion 90 provided at a lower side of the wave-shaped portion 88. The lower end portion 90 has a hook portion 92 which is bent in the inner side. An attachment to be described later is attached on each hook portion 92 of the two arms 70 and 72, and two lower end structures 74 and 76 to be described later in detail are thus formed. The wave-shaped portion 88 has a bellows form. When an opening force to an outer side in the horizontal direction is applied on the hook portion 92, the arm 70 is bent about the wave-shaped portion 88 by this force. At the same time, the arm 72 is similarly deformed. With this process, the two arms 70 and 72 are set in a state where the arms are opened in the short-side direction. The wave-shaped portion 88 is formed as an elastic portion. Because an elastic recovery force is achieved by the elastic portion, when the opening force in the horizontal direction stops acting on the two arms 70 and 72, the two arms 70 and 72 are returned to their original shapes by the above-described elastic recovery force. In other words, the two arms 70 and 72 are set in the closed state.

Figure 9:
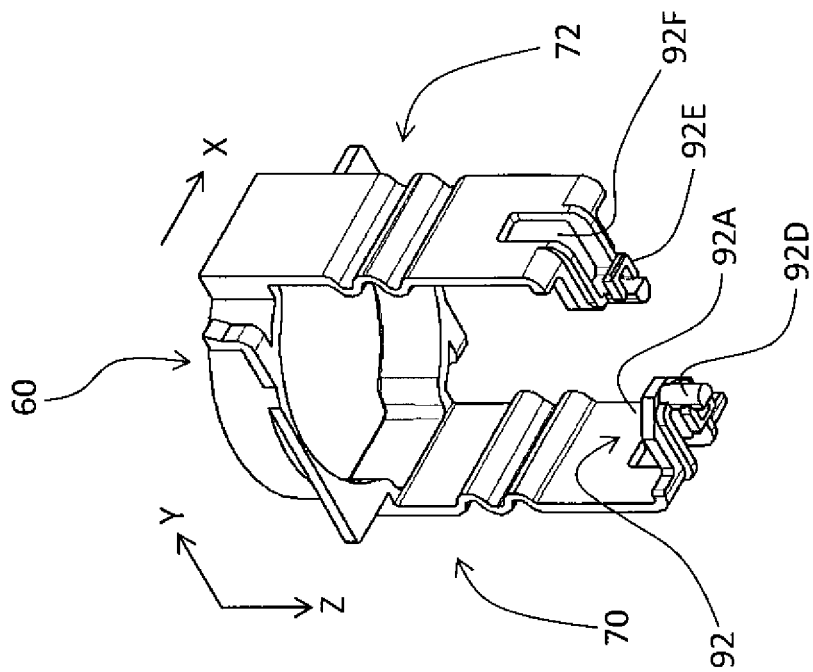
FIG. 9 is a second perspective view of an adapter.

FIG. 9 shows the adapter viewed from diagonally below. As described above, the adapter 60 has the two arms 70 and 72, each of which has the hook portion 92. In the present embodiment, the hook portion 92 has a hook base 92A which is a bent portion and which forms a base surface. The hook base 92A has a U shape when viewed from the above. In the hook base 92A, a contact member 92D extending in the vertical direction is provided. The contact member 92D has a semi-cylindrical shape or a D shape when viewed from above. When the contact member 92D contacts an inclined surface formed in the guide block during a movement of the rack, an opening force is generated toward the outer side in the horizontal direction. A connector 92E is provided below the hook base 92A, and is fixed on the contact member 92D. The connecter 92E has a rectangular shape, and an attachment is detachably attached using the connector 92E. On lower end portions of the arms 70 and 72, an L-shaped channel 92F having an L shape when viewed in the X direction is formed.

Figure 10:
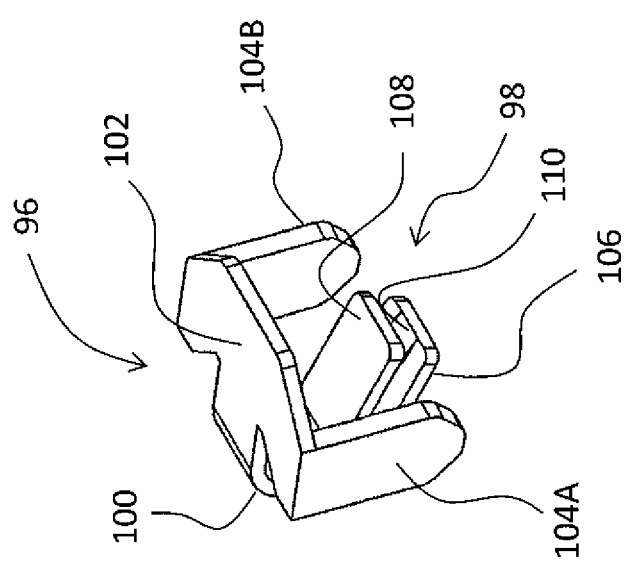
FIG. 10 is a first perspective view of an attachment.

FIG. 10 is a first perspective view of the attachment attached to the body of the adapter. FIG. 10 shows the attachment 96 viewed from diagonally above.

As shown in FIG. 10, the attachment 96 has a connection structure 98 which is connected to the hook portion shown in FIGS. 8 and 9. The connection structure 98 forms a connection end, and more specifically has a lower plate 106 and an upper plate 108. The region between the plates is a slit 110, and the connector shown in FIG. 9 is inserted into the slit 110. In FIG. 10, in the slit 110, a protrusion (not shown) is provided, and the protrusion is fitted into an opening formed in the connector. With this process, the attachment 96 is mounted on the body of the adapter.

A seat plate 102 serving as a movable piece is provided above the connection structure 98. The seat plate 102 forms a contact end, and an upper surface thereof functions as a seat surface. That is, a lower surface of the sample container is placed on the seat plate 102.

A C-shaped arm 100 having a C shape is provided between the connection structure 98 and the seat plate 102. The C-shaped arm 100 functions as an elastic deformation section. In a natural state, the seat plate 102 is in an inclined orientation. When a pressing force is applied on the seat plate 102 from above through the sample container, the C-shaped arm is elastically deformed to absorb the pressing force. In this state, the seat plate 102 is set in a horizontal orientation.

On a right end and a left end of the seat plate 102, a pair of stopper pieces 104A and 104B extending downward are provided. With an up-and-down movement of the seat plate 102, the pair of stopper pieces 104A and 104B also move in the up-and-down direction. Thus, when the seat plate 102 is lowered in the downward direction, the stopper pieces 104A and 104B also are moved in the downward direction, and the lower end positions thereof are further lowered. As a result, as will be described later, even if the lower end structure attempts to move toward the outer side in the horizontal direction, the stopper pieces 104A and 104B collide with the adapter body, and the opening movement of the lower end structure is blocked.

Figure 11:
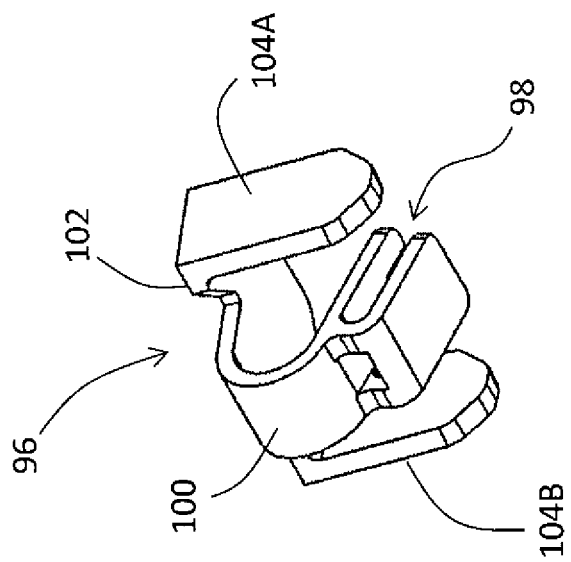
FIG. 11 is a second perspective view of an attachment.

FIG. 11 is a second perspective view of the attachment 96. Specifically, FIG. 11 shows the attachment 96 viewed from diagonally below. As described above, the attachment 96 has the connection structure 98, the C-shaped arm 100, and the seat plate 102. On the right end and the left end of the seat plate 102, the pair of stopper pieces 104A and 104B are provided. Alternatively, the body of the adapter and the attachment may be integrally formed.

Figure 12:
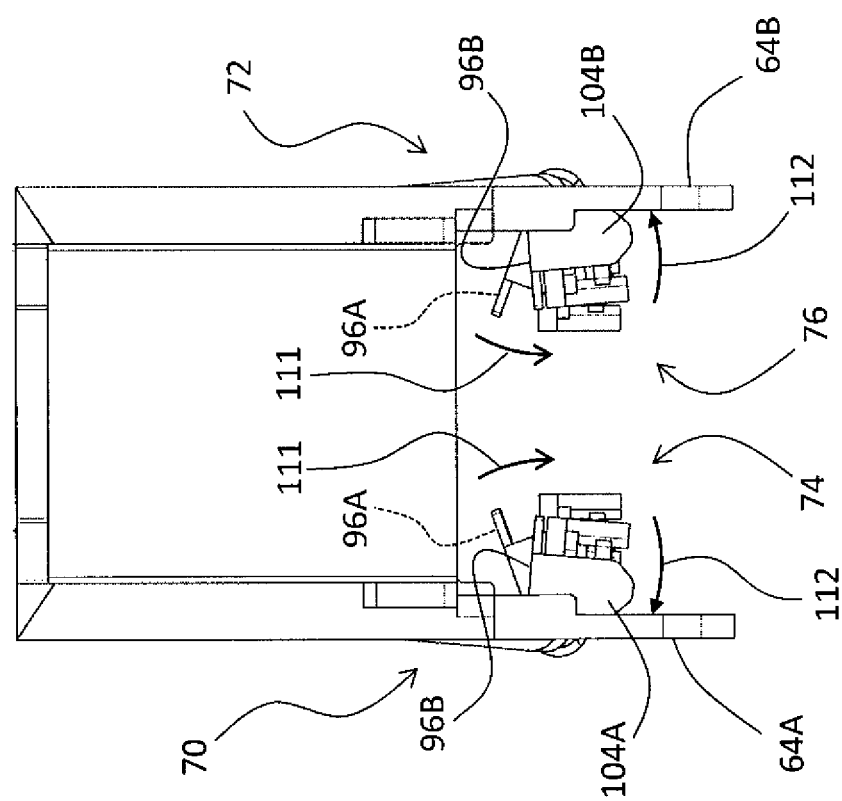
FIG. 12 is an explanatory diagram of an operation of an attachment.

The function of the adapter will now be described with reference to FIGS. 12-17. FIG. 12 is an explanatory diagram for explaining an operation of the adapter. The adapter is attached to the rack body. Arms 70 and 72 have lower end structures 74 and 76. Each of the lower end structures 74 and 76 has the attachment 96. In FIG. 12, an attachment in an inclined orientation before deformation is shown with a reference numeral 96A, and an attachment in a horizontal orientation after the deformation is shown with a reference numeral 96B.

In a state where the sample container is lowered into the storage unit, the seat plates of the pair of attachments contact the lower surface of the sample container. With this configuration, the sample container is supported from below. In this case, as shown with the reference numeral 96A, the seat plates of the attachments are in a lifted state, and two arms are in the closed state.

In the closed state, when an excessive pressing force 111 is applied from above toward below with respect to the sample container, the attachment is deformed as shown with the reference numeral 96B, by the pressing force 111. Specifically, the seat plate in each attachment is lowered downward and is set in the horizontal orientation. At the same time, the stopper pieces 104A and 104B attached to the seat plate are moved downward. On the other hand, due to the pressing force from above, the two arms 70 and 72 attempt to move in a direction away from each other; that is, the opening direction (refer to reference numeral 112). However, because the stopper pieces 104A and 104B are lowered downward along with the seat plate, even when the lower end structures 74 and 76 attempt to pass the lower opening formed in the rack body and move to the outside, the stoppers 104A and 104B collide with the inner surfaces of the legs 64A and 64B, blocking such an opening movement 112. In other words, in the opening movement by the pressing force, the lower end structures 74 and 76 do not protrude to the outside of the rack body through the lower opening, and the holding of the sample container is maintained. While the sample container stores the liquid sample including a radioactive substance, falling of such a sample container from the rack can be reliably prevented.

On the other hand, when the pressing force 111 is not present, only the force due to the weight of the sample container is applied to the attachment. In this case, as shown with the reference numeral 96A, in each attachment, the seat plate maintains the lifted orientation. In such a case, the lower end positions of the stopper pieces 104A and 104B are at the lifted end, and thus, when an opening force to the outer side in the horizontal direction is applied to the lower end structures 74 and 76, protrusion of the lower end structures 74 and 76 to the outside of the rack body through the lower opening formed in the rack body is permitted. In other words, in the pair of the arms, deformation from the closed state to the open state is permitted.

As described, according to the present embodiment, the protrusion of the lower end structures 74 and 76 to the outside of the rack body is permitted only when an appropriate force to the outer side in the horizontal direction is applied from the guide block. When an abnormal force is caused in the vertical direction, the change of the pair of the arms from the closed state to the open state can be prevented by the functions of the stopper pieces 104A and 104B.

Figure 13:
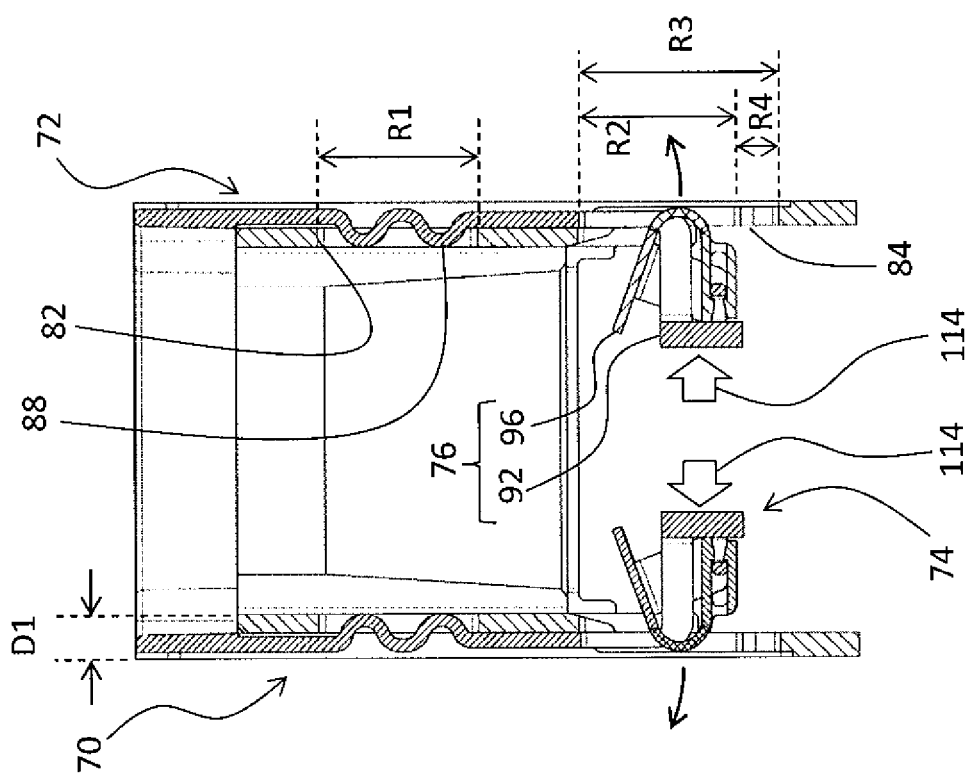
FIG. 13 is a cross sectional diagram of a rack.

FIG. 13 is a cross sectional diagram of the rack. Specifically, FIG. 13 shows a state where the adapter is attached to the rack body. In the arms 70 and 72, a part of the wave-shaped portion 88 is stored in the upper opening shown with R1. The entirety of the arms 70 and 72 is substantially stored in a thick thickness D1 of the rack body, except for the lower end structures 74 and 76. Thus, in the state before the deformation of the arms 70 and 72, no portion in the arms 70 and 72 protrudes from the rack body toward the outer side. With this configuration, even when a specific rack is moved in the longitudinal direction in an aligned state of a plurality of the racks, no hooking occurs that would block the movement.

In a normal closed state where no pressing force from above is applied, when an opening force shown with a reference numeral 114 is applied to the lower end structures 74 and 76 by the contact with the guide block, the lower end structures 74 and 76 move in a direction away from each other, and protrude toward the outer side of the rack through the pair of lower openings.

In FIG. 13, R3 shows a size in the vertical direction of the lower opening 84. R2 shows a size in the vertical direction of a main region of the lower opening 84, and R4 shows a size in the vertical direction of a sub area of the lower opening. When the opening force 114 is applied in the closed state, the lower end structures 74 and 76 pass through the pair of lower openings. On the other hand, when the pressing force from above is caused, the plurality of stopper pieces are lowered downward, and, even when the lower end structures 74 and 76 attempt to move in a direction away from each other, the plurality of stopper pieces collide with the inner surfaces of the pair of legs, and such an opening movement is blocked. This operation will now be further described with reference to FIGS. 14 and 15.

Figure 14:
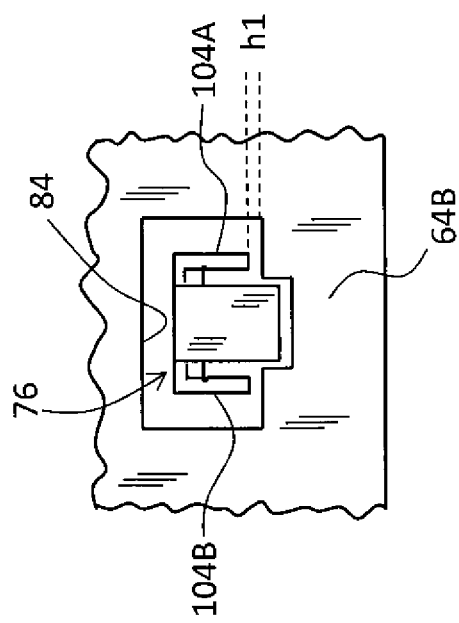
FIG. 14 is a diagram showing a non-operation state of a stopper.

FIG. 14 shows a state where the stopper piece is not operating. In such a case, in the lower end structure 76, the stopper pieces 104A and 104B are in the lifted position, and there is a gap h1 between a lower side level of the main area in the lower opening 84 and the lower end levels of the stopper pieces 104A and 104B. Therefore, the lower end structure 76 can protrude to the outside through the lower opening 84.

Figure 15:
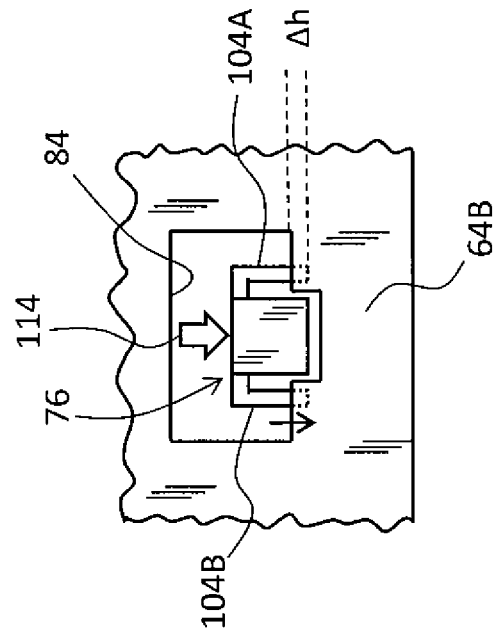
FIG. 15 is a diagram showing an operation state of a stopper.

In the contrary, FIG. 15 shows an operation state of the stopper piece. Specifically, when the pressing force 114 is applied to the lower end structure 76, the stopper pieces 104A and 104B are lowered downward, and the lower end levels thereof become further lower than the lower side level of the main area of the lower opening 84. An overlapped portion in this process is shown in FIG. 15 with Δh. In this state, even when the lower end structure 76 attempts to protrude to the outside through the lower opening 84, the stopper pieces 104A and 104B collide with the inner sides of the leg 64B, and the movement is reliably prevented.

Figure 16:
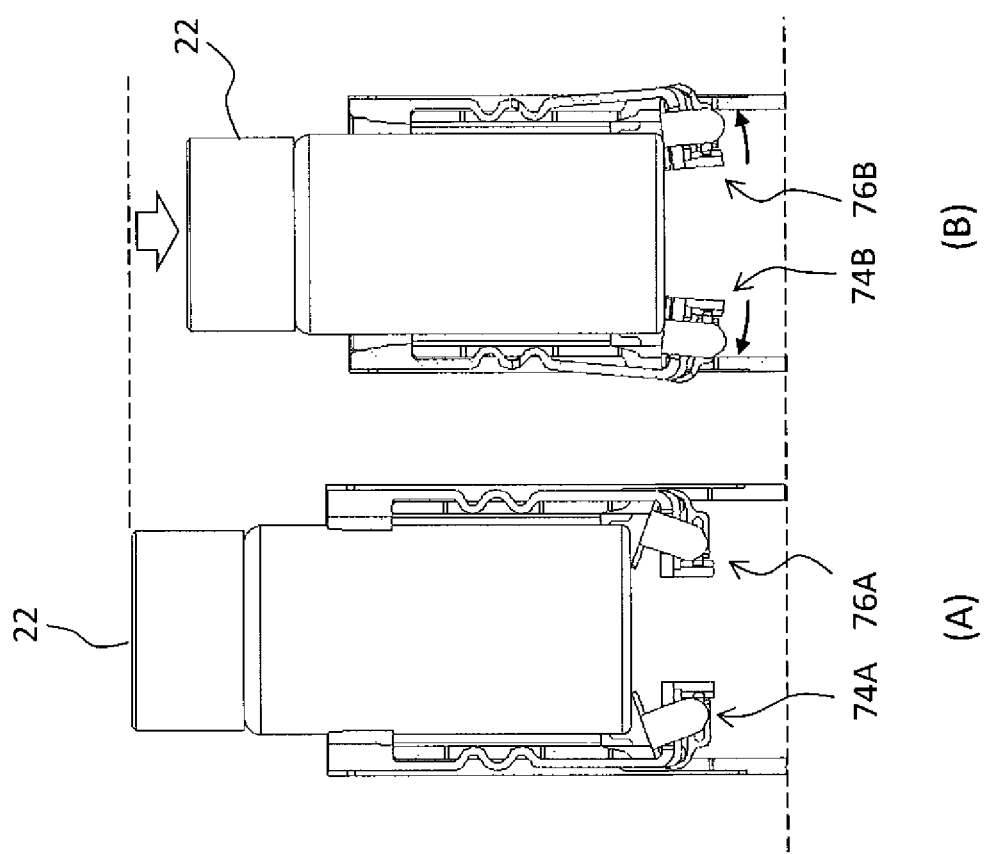
FIG. 16 is an explanatory diagram of an operation of a lower end unit.

FIG. 16 shows a state where the sample container 22 is stored in the rack. Part (A) shows a normal state and part (B) shows a state where the pressing force is caused. Reference numerals 74A and 76A show the lower end structures before deformation and in the lifted state, and reference numerals 74B and 76B show the lower end structures after deformation and in the lowered state.

Figure 17:
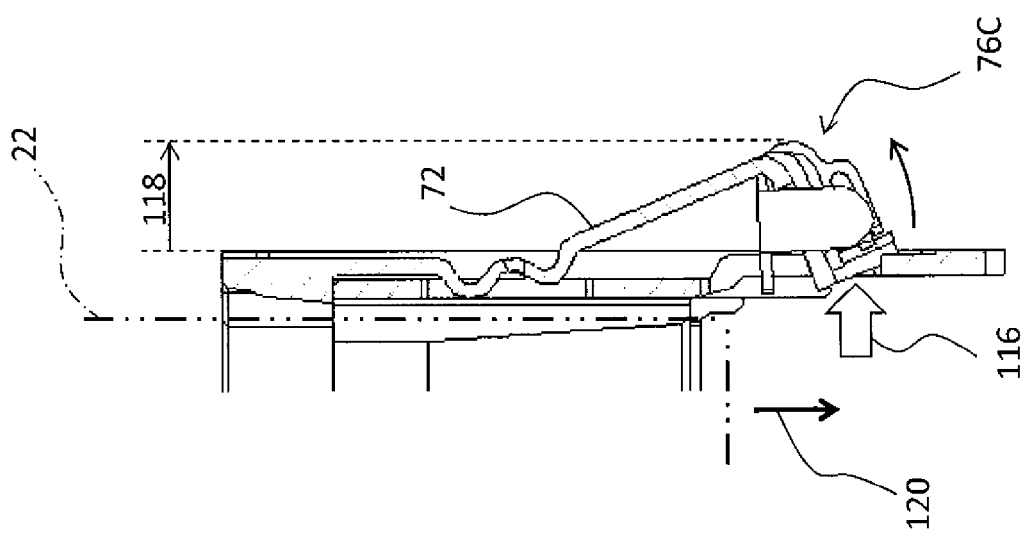
FIG. 17 is a diagram showing an open state of an arm.

FIG. 17 shows an open state of the arm 72. With the movement of the rack in the X direction and contact with the guide block, an opening force 116 in the horizontal direction is applied on the lower end structure. With this process, as described above, the entirety of the arm 72 including the lower end structure is moved in an open movement. The lower end structure in the open state is shown with a reference numeral 76C. In this case, the arm 72 is bent and deformed about the wave-shaped portion in the arm 72. An amount of protrusion of the overall arm 72 from the side surface of the rack is shown by a reference numeral 118. In such an open state, because the supporting function with respect to the lower surface of the sample container 22 disappears, if there is no member below the sample container 22, the sample container 22 naturally falls below as shown by a reference numeral 120. In the present embodiment, in such an open state, the sample container 22 is placed on the head.

When the sample container is moved from the rack to the head, the pair of lower end structures is moved from a position immediately below the sample container to a retracted position in an outer side in the horizontal direction. Then, after the sample container after the sample measurement is returned to the inside of the sample storage unit, the pair of the arms is returned to the original shape. That is, the pair of lower end structures enter the lower side of the sample container. With this configuration, the sample container 22 is supported by the pair of the lower end structures, and is held.

As described, according to the present embodiment, in each storage unit, the open/close mechanism can be transitioned from the closed state to the open state at an appropriate timing. In addition, when an abnormal pressing force in the vertical direction is caused in place of the appropriate opening force, unnecessary opening movement is reliably prevented by the function of the plurality of stopper pieces as described above. With such a configuration, falling of the sample container can be prevented beforehand. Further, an elastic deformation section is provided in each arm, and, with the elastic recovery force achieved thereby, the arm can be returned to its original shape. Therefore, the transition from the open state to the closed state can be achieved by the function of the arm itself. According to the present embodiment, no dedicated drive source and no dedicated controller are necessary for the opening operation of the pair of the arms. In addition, no dedicated drive source and no dedicated controller are necessary for the closing operation of the pair of the arms. The pair of the arms can be opened and closed using a part of the transporting force of the rack and in synchronization with the transportation of the rack.

(C) Guide Block (FIGS. 18-23)

Figure 18:
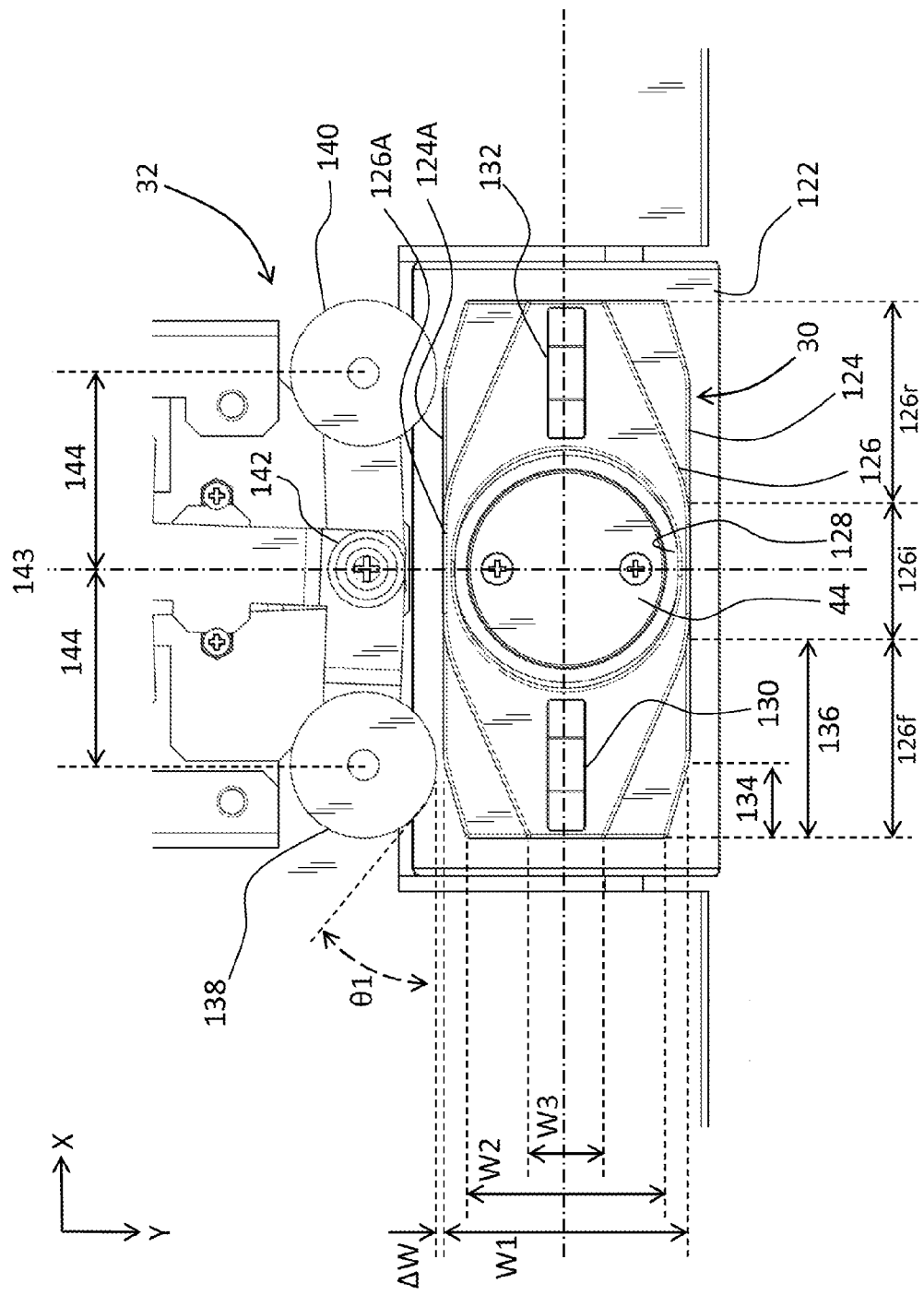
FIG. 18 is an enlarged top view of a guide block.

FIG. 18 shows a part of the transport table as an enlarged top view. Specifically, FIG. 18 shows the guide block 30 and the pressing unit 32.

The guide block 30 is fixedly placed on a top frame 122. The top frame 122 corresponds to a top plate of a structure including the lifting/lowering path. The guide block 30 has a lower layer 124, an upper layer 126, a front-side support plate 130, and a rear-side support plate 132. These elements are integrated. Each of the lower layer 124 and the upper layer 126 has a flat plate shape spreading in the horizontal direction. The front-side support plate 130 and the rear-side support plate 132 have a form standing upwards. At the center of the guide block 30, an opening 128 is formed. The opening 128 has a circular or elliptical shape. The opening 128 forms an upper end of the lifting/lowering path, and, in FIG. 18, the head 44 is inserted into the opening 128. A width W1 in the Y direction of the lower layer 124 is approximately the same as a gap between the pair of legs of the rack. Strictly speaking, the width W1 is slightly smaller than the gap. On each of a front end portion (left end portion in FIG. 18) and a rear end portion (right end portion in FIG. 18) of the lower layer 124, a pair of inclined surfaces 134 are formed. In other words, the lower layer 124 has a shape tapered in both directions. A width in the Y direction of a front surface and a rear surface of the lower layer 124 is W2, and W1>W2. Because the pair of inclined surfaces 134 are formed on the front end portion in this manner, even if there is a position deviation in the Y direction for the rack side in the process of entry of the guide block 30 into a region between the pair of legs, the position deviation can be resolved. In addition, a pair of inclined surfaces are also formed on the rear end portion of the lower layer 124. With such a configuration, even if it becomes necessary to return-transport the rack, the guide block 30 can be smoothly inserted into the lower part of the rack from the rear side of the rack.

The upper layer 126 is a portion layered on top of the lower layer 124, and a pair of inclined surfaces 136 are formed with a relatively long distance at a front-side portion (front-side form 126f) of the upper layer 126. A width in the Y direction of the front end surface in the upper layer 126 is W3. Here, W1>W2>W3. The pair of inclined surfaces 136 are provided such that the width in the Y direction of the upper layer 126 continuously changes from W3 to W1 along the X direction.

When the pair of contact members of the pair of open/close mechanisms contacts the pair of inclined surfaces 136, and the rack is moved forward while the contact state is maintained, an opening force to the outer side in the horizontal direction is applied on the pair of contact members by the function of the pair of inclined surfaces 136. With this process, the adapter is changed from the closed state to the open state. In the present embodiment, a pair of inclined surfaces are also formed on the rear-side portion (rear-side form 126f) of the upper layer 126. With the pair of the inclined surfaces on the rear side, the recovery from the open state to the closed state can be gradually achieved, thus preventing a rapid change of the open/close mechanism.

In the present embodiment, the pair of inclined surfaces 136 on the front side and the pair of inclined surfaces on the rear side formed on the upper layer 126 have a symmetrical shape, but alternatively, these surfaces may have an asymmetrical shape.

The guide block 30 can be roughly divided from the upstream side to the downstream side of the X direction, into a front-side form, an intermediate form, and a rear-side form. Looking into the upper layer 126, the front-side form 126f of the upper layer 126 realizes the function to change the open/close mechanism from the closed state to the open state. The intermediate form 126i of the upper layer 126 realizes a function to maintain the open state. The rear-side form 126r of the upper layer 126 realizes a function to return the open/close mechanism from the open state to the closed state. The guide block 30 as a whole has a symmetrical shape with reference to a center line passing through a center position in the Y direction and parallel to the X direction. In a state where the guide block 30 enters a region between the pair of legs of the rack, centering (positioning in the Y direction) of the rack is executed. With this process, the center position of the opening 128 and the center position of the sample container to be measured or a sample storage unit that stores the sample container can be easily matched in the Y direction.

In the present embodiment, as described above, the guide block 30 is fixed on the top frame 122 of the structure including the sample measurement chamber and the lifting/lowering mechanism. The guide block 30 is placed with a certain degree of freedom in the horizontal direction with respect to the transport table. In other words, so long as the guide block 30 is appropriately positioned, it becomes unnecessary to strictly position the transport table itself. For example, even if there is a machining error or an assembly error in the transport table, if the error is within an allowable range, such an error would not cause a problem in the handing of the sample container between the rack and the lifting/lowering mechanism.

In the process of change of the open/close mechanism from the closed state to the open state with the function of the pair of inclined surfaces 136 formed on the front side of the guide block, the supporting function of the sample container by the open/close mechanism disappears. If the support function disappears before the bottom surface of the sample container is sufficiently placed on the head 44, there is a possibility of fall-off or change of orientation of the sample container. In consideration of this, in the guide block 30 according to the present embodiment, the front-side support plate 130 is provided. The front-side support plate 130 has a form protruding upward from the upper surface of the upper layer 126. The front-side support plate 130 realizes a function to support the sample container temporarily and in an auxiliary manner in a state where the supporting function of the sample container by the open/close mechanism has disappeared. A front end and a rear end of the front-side support plate have tapered surfaces of a shoulder shape, such that hooking of a corner portion of the sample container on the front-side support plate is prevented. By preparing an auxiliary support on the front side of the opening 128 in this manner, it becomes possible to prevent fall-off or orientation change of the sample container, and to smoothly transfer the sample container from the rack to the upper surface of the head.

In the present embodiment, the rear-side support plate 132 is provided on the rear side of the opening 128. The rear-side support plate 132 has a form similar to that of the front-side support plate 130. With the rear-side support plate 132, in a case where, after the sample container after the measurement is returned to the storage unit and in a period until the open/close mechanism returns from the open state to the closed state, if the support function by the upper surface of the head 44 partially disappears, the sample container can be temporarily supported in an auxiliary manner by the upper surface of the rear-side support plate 132, to prevent fall-off and orientation change of the sample container.

As described, according to the guide block 30 of the present embodiment, an opening force to the outer side in the horizontal direction can be applied to each open/close mechanism using a part of the rack transporting force. Therefore, because it is not necessary to provide a dedicated drive source or a dedicated drive mechanism for producing such an opening force, there is an advantage that the device structure can be simplified. In addition, the operation timing of each open/close mechanism can be naturally matched with respect to a reference position, and there is an advantage that it is not necessary to control the opening/closing by a controller. Furthermore, because the guide block 30 is placed with reference to the reference position itself, the rack can be centered merely by inserting the guide block 30 between the pair of the legs of the rack. In other words, the sample container or the storage unit having the sample container can be appropriately positioned with respect to the reference position by merely inserting the guide block 30 to the lower part of the rack.

FIG. 18 also shows the pressing unit 32 in addition to the guide block 30. A structure of the pressing unit 32 will now be described. The structure and an operation of the pressing unit 32 will again described later with reference to FIGS. 24-26.

In FIG. 18, the pressing unit 32 is a unit which applies a pressing force on the rack from the outside of the rack, to realize appropriate position and orientation of the rack. In the present embodiment, the pressing unit 32 has a pair of rollers 138 and 140 as a first contact member and a second contact member which contact the rack and apply the pressing force. A rotational center of the roller 138 is set at a point distanced from the reference position 143 by a certain distance 144 in the upstream side; that is, the front side, in the X direction. A rotational center of the roller 140 is set at a point distanced from the reference position 143 by the certain distance 144 in the X direction.

As will be described later, the roller 138 is rotatably attached on an end of one movable plate, and the roller 140 is attached to an end of the other movable plate. A common rotational axis of the movable plates is shown with a reference numeral 142. In the Y direction, the rotational centers of the rollers 138 and 140 are set farther away from the guide block 30 with respect to a rotational center of the common rotational axis 142. In other words, a negative offset is given to the rotational centers.

Reference surfaces are formed in the guide block 30 for cooperation with the pressing unit 32 to achieve appropriate position and orientation of the rack. Specifically, reference surfaces 124A and 126A are formed. The reference surface 124A is one side surface of the lower layer 124 and the reference surface 126A is one side surface of the upper layer 126. In the present embodiment, the reference surfaces 124A and 126A are surfaces parallel in the X direction, and are vertical surfaces. Of the two reference surfaces 124A and 126A, the reference surface 124A spreads wider in the X direction. When the guide block enters a region between the pair of legs of the rack, the pair of rollers 138 and 140 are pressed against the outer surface of one leg (leg on the side of the pressing unit 32) of the pair of legs. With this process, the inner surface of the one leg closely contacts the reference surfaces 124A and 126A. The reference surfaces are vertical surfaces parallel in the X direction, and the inner surfaces of the pair of legs are vertical surfaces parallel in the longitudinal direction. Thus, in a state where the inner surface is in close contact with the reference surface, the X direction and the longitudinal direction of the rack become parallel to each other. At the same time, the rack is positioned at a predetermined position in the Y direction. As a result, appropriate position and orientation of the rack can be realized.

In the present embodiment, in an initial state of the rollers 138 and 140, there is a certain gap ΔW between the respective roller and the reference surfaced 124A. Such a gap ΔW is provided as necessary. In the present embodiment, with the gap ΔW and the negative offset of the roller 138, an angle θ1 for receiving a tip portion of one leg is increased, or a resistance when the tip portion is received is reduced. With the function of the inclined surface 134 and such an open angle θ1, even if there is a position deviation in the Y direction in the rack, the one leg can be smoothly inserted between the reference surface 124A and the roller 138.

In a state where the guide block 30 is inserted between the pair of legs as described above, a pressing force is applied from the rollers 138 and 140 on the outer surface of the one leg. With this process, the inner surface of the one leg closely contacts the reference surfaces 124A and 126A. Therefore, an appropriate position (in particular, a position in the Y direction) and an appropriate orientation of the rack can be achieved with a simple mechanism. In the present embodiment, because the rollers 138 and 140 are provided as the pressing member, even when the rack is sent toward the front side, a sliding resistance can be reduced.

In the present embodiment, the pressing unit 32 presses the rack with respect to the guide block 30 placed at the appropriate position and orientation. Thus, even if there is a machining error or an assembly error in the transport table, the rack can be accurately positioned with respect to the reference position. In addition, in the present embodiment, the rollers 138 and 140 are provided with an equal spacing in the front-and-rear direction from the reference position in the X direction. Therefore, a force can be equally applied on both sides of the reference position on the rack. Even if there is a deflection in the rack, in the present embodiment, the pressing is applied in a range in the X direction where the guide block 30 exists, and thus, even with the deflection, the sample container to be measured can be appropriately positioned with respect to the reference position.

A description of a function of the guide block will be continued with reference to FIGS. 19-23.

Figure 19:
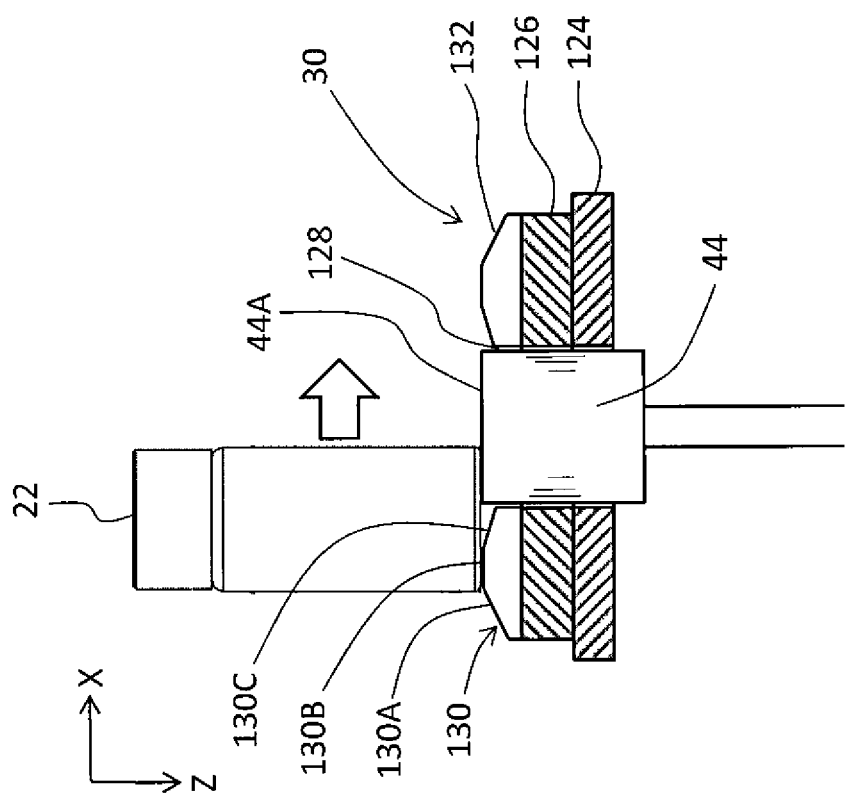
FIG. 19 is a cross sectional diagram of a guide block.

FIG. 19 shows a cross sectional diagram of the guide block 30. As described above, the guide block 30 has the upper layer 124, the lower layer 126, the front-side support plate 130, and the rear-side support plate 132. In FIG. 19, each member is shown as a separate member, but in the present embodiment, the members are integrated. The front-side support plate 130 has an upper surface 130B, and inclined surfaces 130A and 130C provided in front of and to the rear of the upper surface 130B. The rear-side support plate 132 has a structure similar to that of the front-side support plate 130.

The opening 128 penetrating through the guide block 30 in the up-and-down direction is formed at a center of the guide block 30. In FIG. 19, the head 44 is inserted into the opening 128. The head 44 has a placement surface 44A serving as an upper surface, and the sample container 22 is placed on the placement surface 44A. As shown in FIG. 19, in the process of transition from the closed state to the open state of the open/close mechanism, the sample container 22 is supported in an auxiliary manner by the upper surface 130B of the front-side support plate 130. As a result, the sample container 22 can be smoothly transferred onto the placement surface 44A. During the transfer, it is desirable that a level of the placement surface 44A of the head 44 and a level of the upper surface 130A are substantially matched. Alternatively, one of these surfaces may be slightly above or below the other surface.

Figure 20:
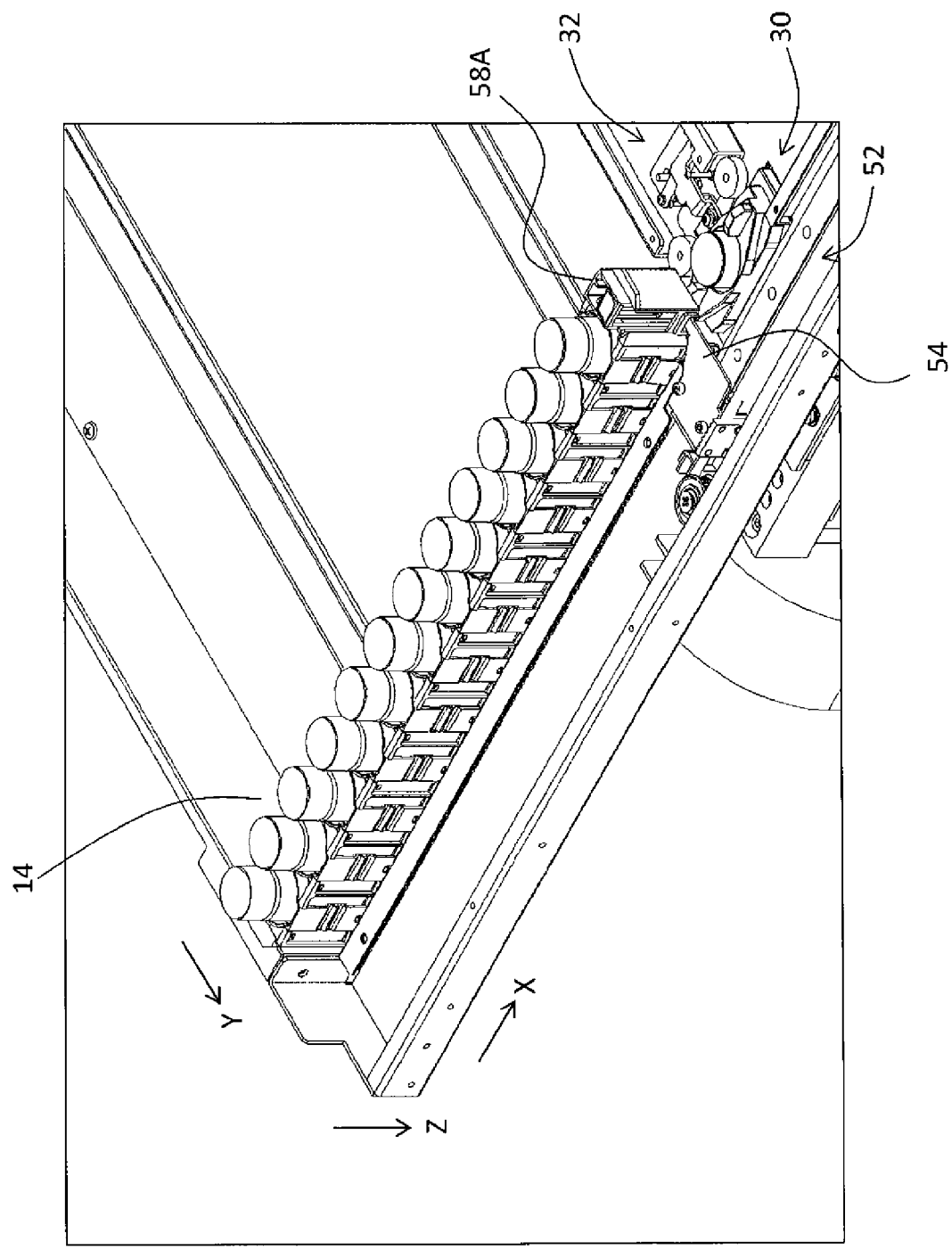
FIG. 20 is a perspective view showing a rack introduction state to an X transport path.

FIG. 20 shows a state where the rack 14 is introduced to the X transport path. As described above, the rack 14 has the protrusion 58A, and a part of the hook member 54 of the transporting mechanism 52 is inserted to the protrusion 58A. The guide block 30 is provided at the center of the X transport path, and the pressing unit 32 is provided nearby.

Figure 21:
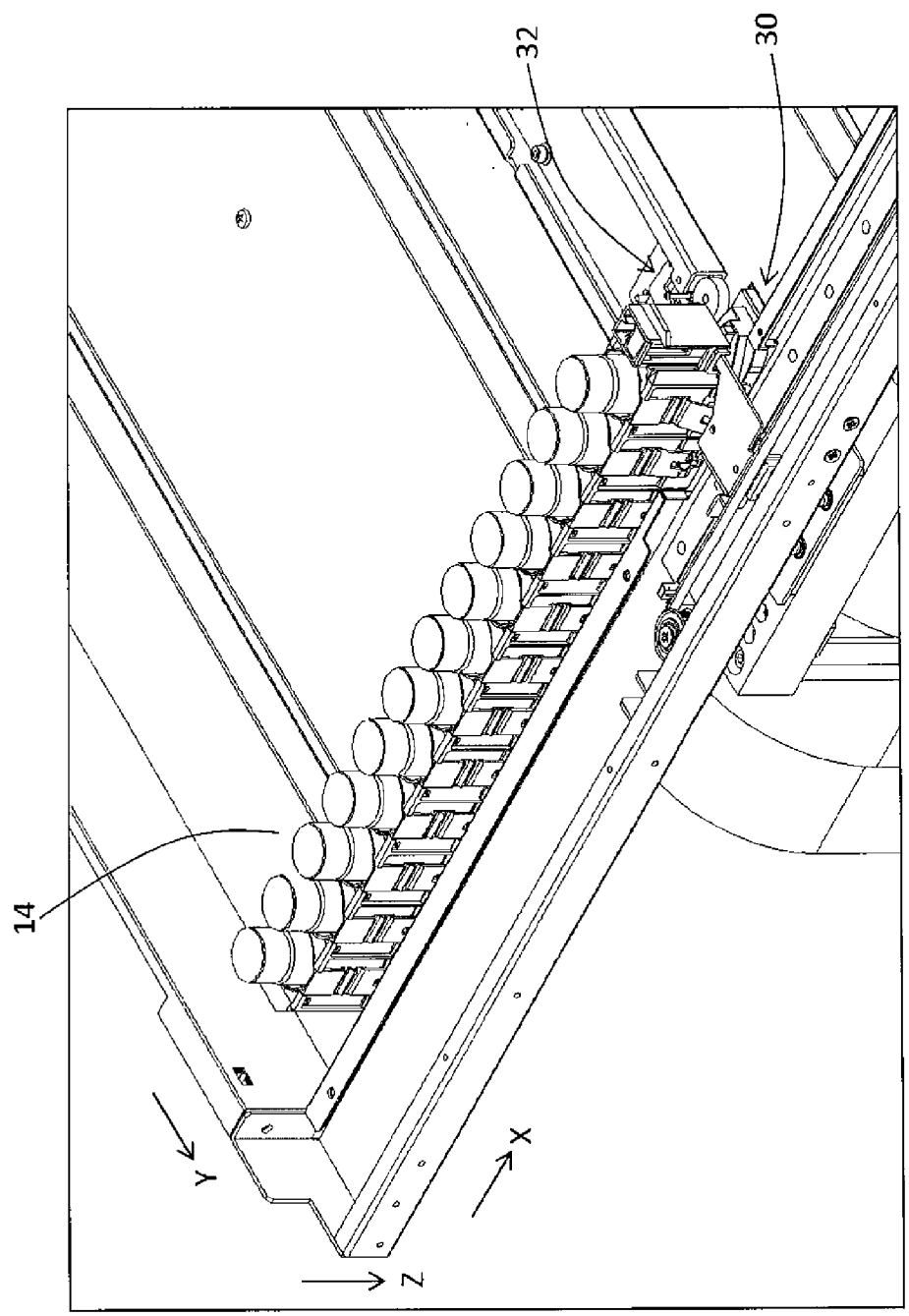
FIG. 21 is a perspective view showing a handing state of a sample container.

FIG. 21 shows a state where the rack 14 is progressed on the X transport path. Specifically, FIG. 21 shows a state where the front-most sample container is positioned with respect to the opening of the guide block 30. In this state, the pressing unit 32 functions, and an appropriate position and an appropriate orientation of the rack 14 are realized.

Figure 22:
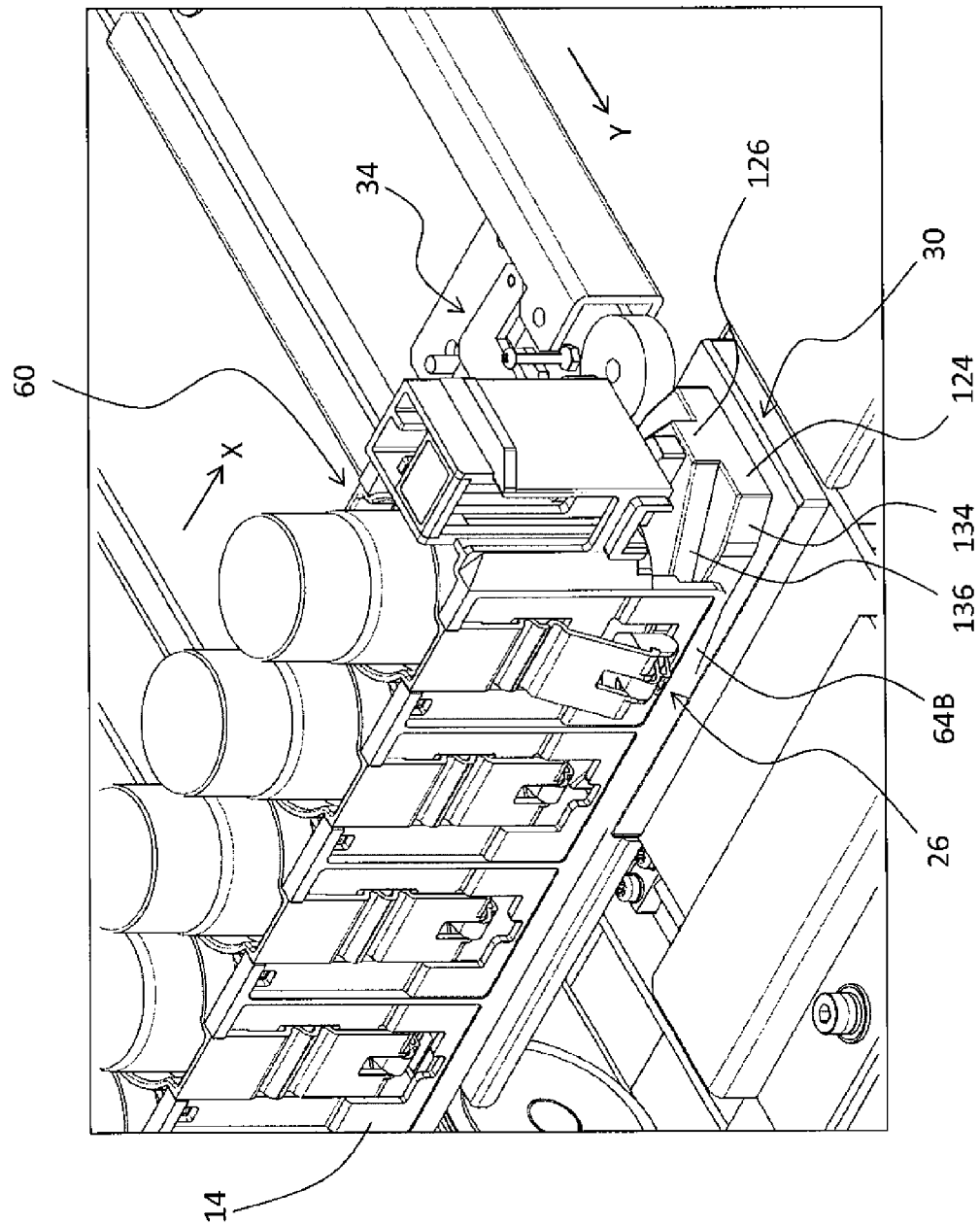
FIG. 22 is an enlarged perspective view showing a handing state of a sample container.

FIG. 22 shows a part of the contents shown in FIG. 21 as an enlarged view. The rack 14 has a plurality of storage units, and the adapter 60 is attached in each storage unit. The adapter 60 has the open/close mechanism 26. In FIG. 22, only one open/close mechanism 26 is set in the open state. The guide block 30 functions to form such an open state. As described above, the guide block 30 has the lower layer 124, the upper layer 126, etc. The guide block 30 is inserted between the pair of legs in the rack 14. In FIG. 22, only the leg 64B on the other side is shown. On the rear side of the lower layer 124, the pair of inclined surfaces 134 is formed, and on the rear side of the upper layer 126, the pair of inclined surfaces 136 is formed. In the front-side portions of the lower layer 124 and the upper layer 126 also, the pair of inclined surfaces are formed. In the state shown in FIG. 22, the pressing force in the Y direction is applied on the rack by the pressing unit 34, so that the appropriate position and orientation of the rack 14 are achieved and stabilized.

Figure 23:
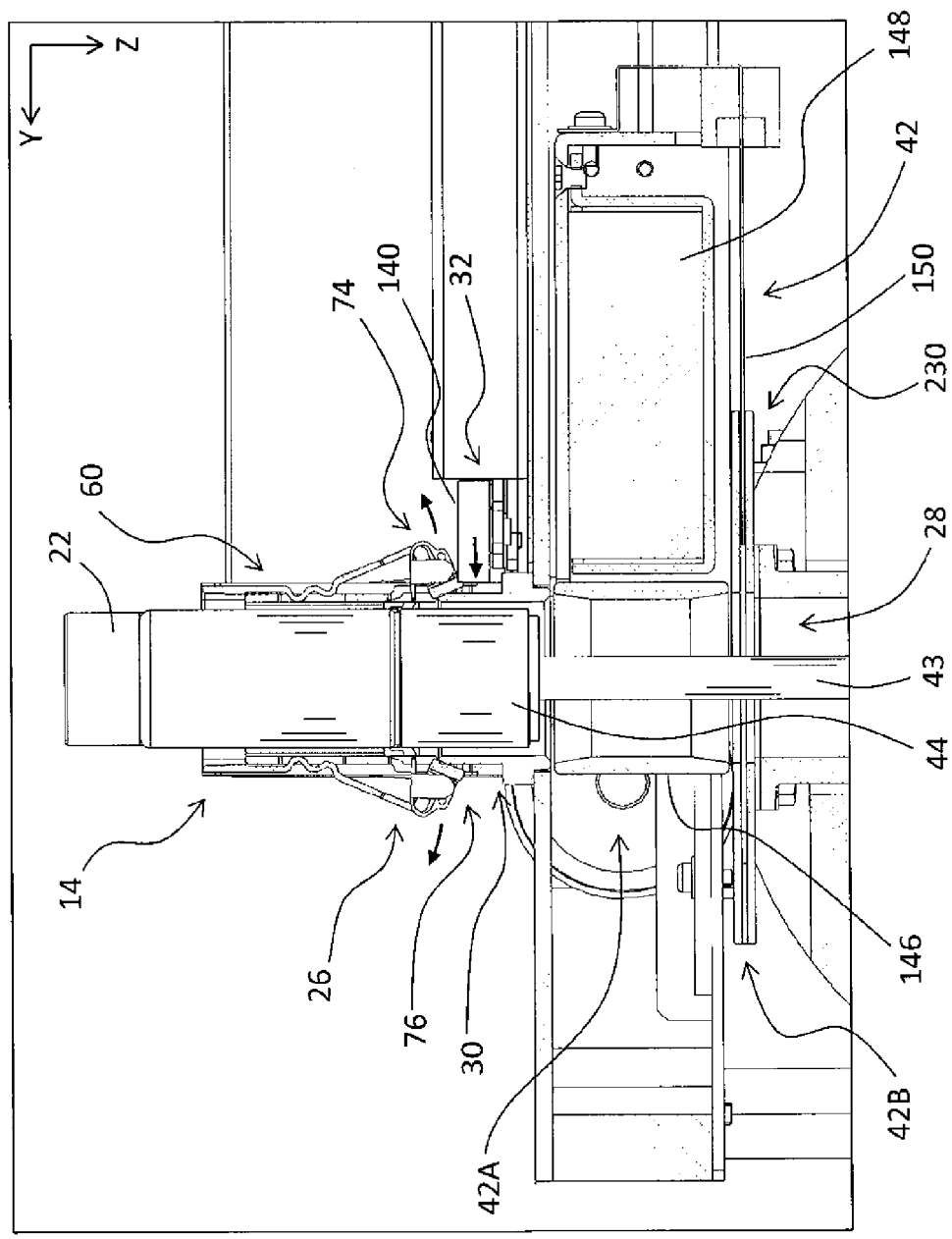
FIG. 23 is a cross sectional diagram showing a handing state of a sample container.

FIG. 23 is a YZ cross sectional diagram of a portion shown in FIG. 22. FIG. 23 includes a cross section of the guide block 30. As described above, in the rack 14, the adapter 60 is provided in each storage unit, and the sample container 22 is stored inside the storage unit. In the state shown in FIG. 23, the open/close mechanism 26 is in the open state, and thus, the lower end structures 74 and 76 protrude from the rack body in both sides in the horizontal direction. Such a function is caused by the pair of contact members of the lower end structures 74 and 76 contacting the pair of inclined surfaces of the guide block 30.

In FIG. 23, a pressing force is applied from the pressing unit 32 to the rack 14 such that the position and orientation of the rack 14 are stabilized. The lifting/lowering path 28 is formed on the lower side of the guide block 30. As already described, the lifting/lowering mechanism has the shaft 43 and the head 44. These elements move in the up-and-down direction inside the lifting/lowering path 28.

As shown in FIG. 23, the shutter mechanism 42 is provided below the guide block 30 across the lifting/lowering path 28. The shutter mechanism 42 will now be briefly described. The shutter mechanism will be again described later with reference to FIGS. 34-36.

The shutter mechanism 42 includes an upper shutter mechanism 42A and a lower shutter mechanism 42B. The upper shutter mechanism 42A is a mechanism for blocking extrinsic radiation from above, and the lower shutter mechanism 42B is a mechanism for blocking extrinsic light entering through the lifting/lowering path 28.

Specifically, the upper shutter mechanism 42A has a lead block 148. With the lead block 148 covering the upper side of the sample measurement chamber across the lifting/lowering path 28, the extrinsic radiation (in particular, cosmic rays or the like) directed toward the sample measurement chamber through the lifting/lowering path 28 is blocked. Portions of the sample measurement chamber other than the lifting/lowering path 28 are basically covered with a shielding member. Alternatively, when the blockage of the space ray is the objective, the placement of the shielding member on the lower side of the sample measurement chamber may be omitted.

The upper shutter mechanism 42A has a tube guide 146. The tube guide 146 is positioned on the lifting/lowering path 28 when the lead block 148 is in the retracted position, and realizes a guide function with respect to the head 44 and the sample container 22 in this state. In the state where the lead block 148 is moved forward, the tube guide 146 moves to a position retracted from the lifting/lowering path 28. The tube guide 146 is a hollow member similar to a sleeve, and has an alignment function as will be described later.

The lower shutter mechanism 42B has a light-shielding plate 150 and a slit structure 230. When the light-shielding plate 150 is moved forward, a part of the light-shielding plate 150 is inserted into a slit of the slit structure 230, and, with this process, the light-shielding plate 150 is placed across the lifting/lowering path 28. In this state, the extrinsic light from above is blocked by the light-shielding plate 150.

As described, according to the guide block, the open/close mechanism can be opened using a part of the drive force for transporting the rack in the X direction. Therefore, there is an advantage that it is not necessary to provide a dedicated drive source for such an opening operation. In addition, when the guide block is inserted between the pair of legs, an appropriate position of the rack in the Y direction can be achieved. That is, the centering can be realized naturally. In addition, because the guide block of the present embodiment has a member which supports in an auxiliary manner the lower side of the sample container in a halfway state between the open state and the closed state, it is possible to prevent disturbance in the orientation or the like of the sample container during the operation of the open/close mechanism. Further, the guide block 30 of the present embodiment has the reference surface which functions with the pressing unit, and, with the cooperation of these elements, the appropriate position and orientation of the rack can be easily realized.

(D) Pressing Unit (FIGS. 24-27)

Figure 24:
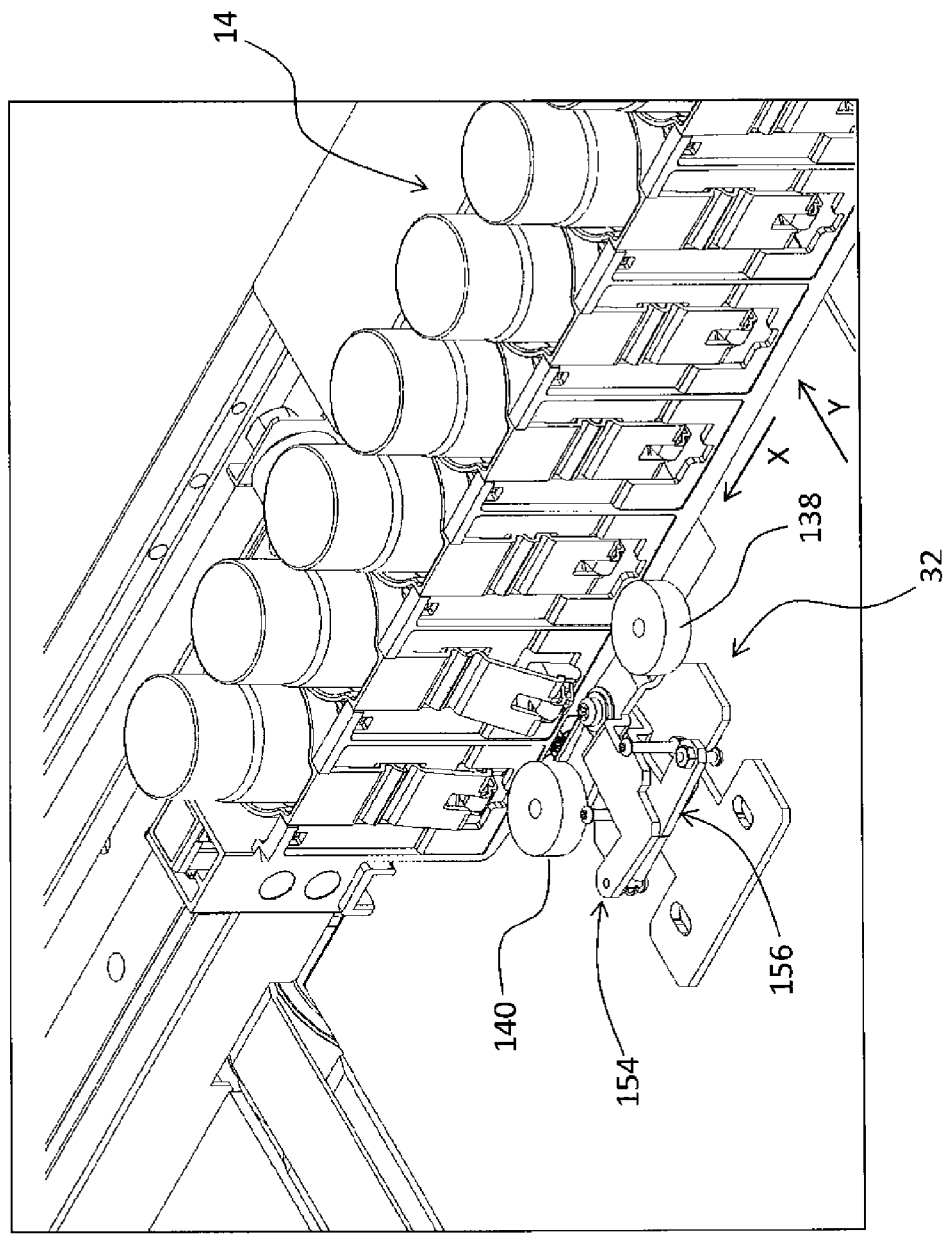
FIG. 24 is a diagram showing an operation state of a pressing unit.

FIG. 24 shows an operation state of the pressing unit 32 as a perspective view. When the rack 14 is transported in the X direction, the pressing unit 32 realizes its function on the left side in the direction of movement of the rack 14. As described above, the pressing unit 32 has the pair of rollers 138 and 140. In order to give an elastic urging force to the pair of rollers, a first movable plate 154 and a second movable plate 156 are provided.

Figure 25:
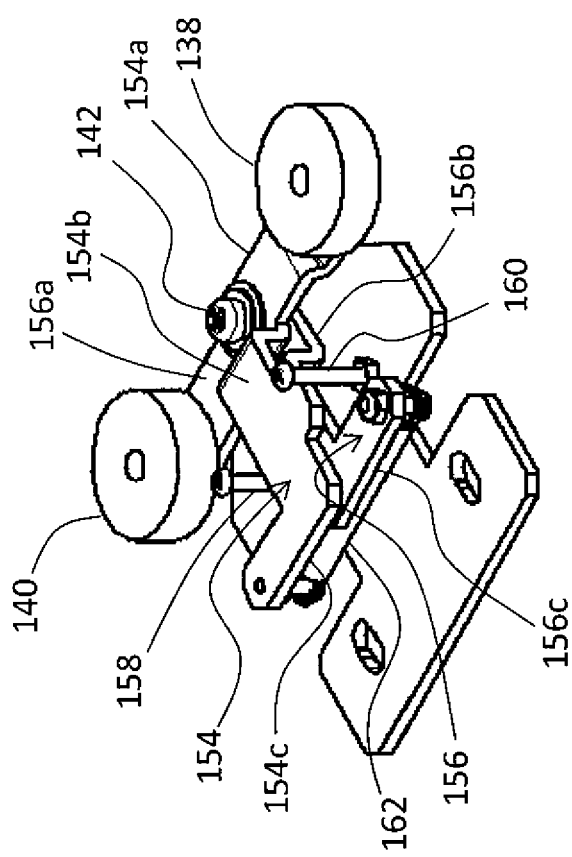
FIG. 25 is a first enlarged perspective view of a pressing unit.

FIG. 25 is a first perspective view of the pressing unit. The first movable plate 154 is an upper plate, and the second movable plate 156 is a lower plate. The plates 154 and 156 rotate about the common rotational axis 142. The first movable plate 154 has a crank shape and the second movable plate 156 also has a crank shape.

The first movable plate 154 has a front-side bent portion 154a, an intermediate portion 154b, and a rear-side bent portion 154c. The roller 138 is rotatably attached to an end of the front-side bent portion 154a. The second movable plate 156 has a front-side bent portion 156a, an intermediate portion 156b, and a rear-side bent portion 156c. The roller 140 is rotatably provided on an end of the front-side bent portion 156a. A pin 160 is a restriction member for preventing unnecessary excessive rotation of the first movable plate 154 in a counterclockwise direction as viewed from above. Similarly, a pin 158 is a restriction member for preventing unnecessary excessive rotation of the second movable plate 156 in the clockwise direction as viewed from above.

Figure 26:
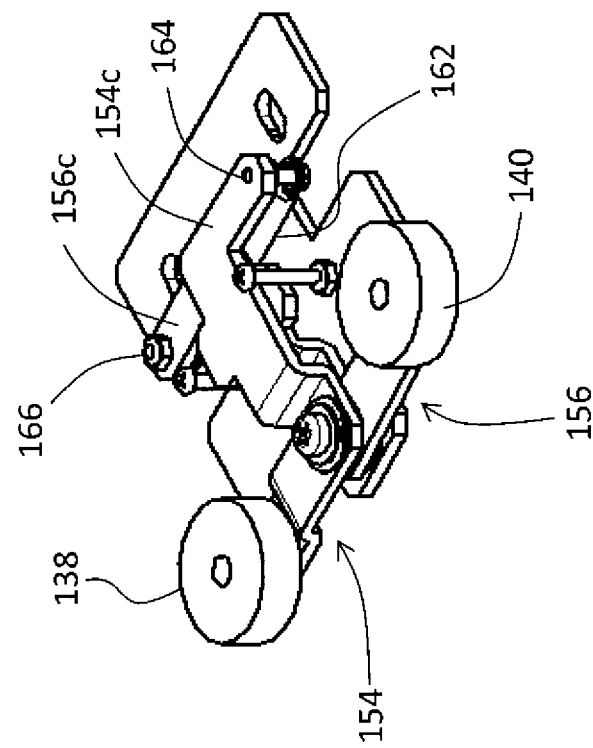
FIG. 26 is a second enlarged perspective view of a pressing unit.

FIG. 26 is a second perspective view of the pressing unit. As described above, the first movable plate 154 has the rear-side bent portion 154c, and a movement axis 164 is provided at an end thereof. The second movable plate 156 has the rear-side bent portion 156c, and a movement axis 166 is provided at an end thereof. A spring 162 is provided in a state of being extending more than in the natural state, between the movement axis 164 and the movement axis 166. In other words, an elastic recovery force is caused at all times in the spring 162, which is transmitted to the pair of rollers 138 and 140 through the first movable plate 154 and the second movable plate 156. With this configuration, the pressing force to the rack is produced. However, as described above, the rotational angles of the plates 154 and 156 in the initial state are restricted by the pair of restriction pins. With this configuration, the gap ΔW shown in FIG. 18 is set.

Figure 27:
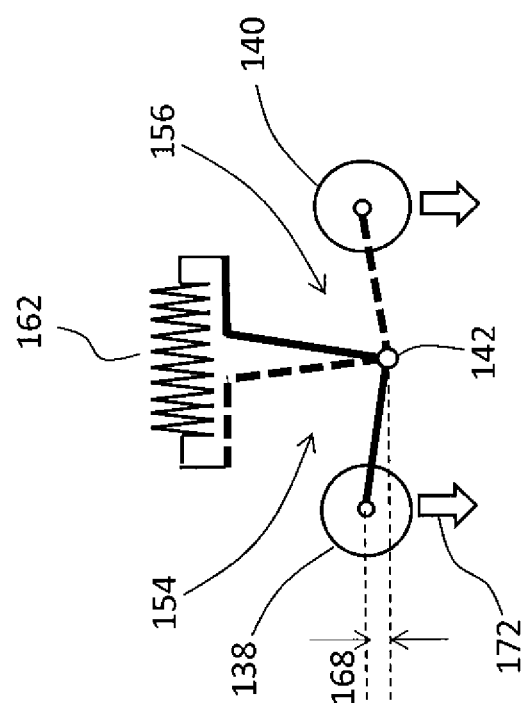
FIG. 27 is a diagram for explaining a function of a pressing unit.

FIG. 27 is a diagram showing a function of the pressing unit. A negative offset 168 is set for the centers of rotation of the rollers 138 and 140 with respect to the center of the common rotational axis 142. That is, the centers of rotation of the rollers 138 and 140 are shifted in the Y direction in a direction farther away from the guide block, relative to the center of the rotational axis 142. The spring 162 is placed between the first movable plate 154 and the second movable plate 156, and, when the rollers 138 and 140 move in a direction away from the guide block, the spring is extended, and a stronger elastic urging force is produced as a reaction force. With this configuration, the pressing force 172 which presses the rollers 138 and 140 toward the side of the rack is produced.

In the present embodiment, because the spring 162 is placed between the two movable plates, in the state where the leg is entered only in the region between the roller 138 and the reference surface, a weak pressing force F1 can be produced, and when the legs are entered in the regions between the two rollers 138 and 140 and the reference surface, a strong pressing force F2 which is a sum of the forces for the two rollers 138 and 140 can be produced. In other words, a gradational force can be realized according to the situation of the entrance. In the initial state where the leg is not entered between the roller 138 and the reference surface, a gap ΔW is formed in the region, and thus, the force applied on the leg when the leg enters the region (reaction force, impact force) can be reduced as compared to a case where the gap is not formed.

According to the pressing unit as described above, as described with reference to FIG. 18, the pressing force can be applied to the outer surface of one leg so that the inner surface of the one leg is in close contact with the reference surface of the guide block. In addition, in this case, because the rollers 138 and 140 are placed to have the negative offset 168, as shown in FIG. 18, an advantage can be obtained in which the open angle for receiving the one leg can be set relatively large. In other words, the rotational movement of the first movable plate can be executed smoothly. Moreover, because in the present embodiment the spring is placed between the two movable plates, the pressing force can be gradationally increased according to the state of sandwiching.

(E) Structure of Lower Side of Transport Surface (FIGS. 28-33)

Figure 28:
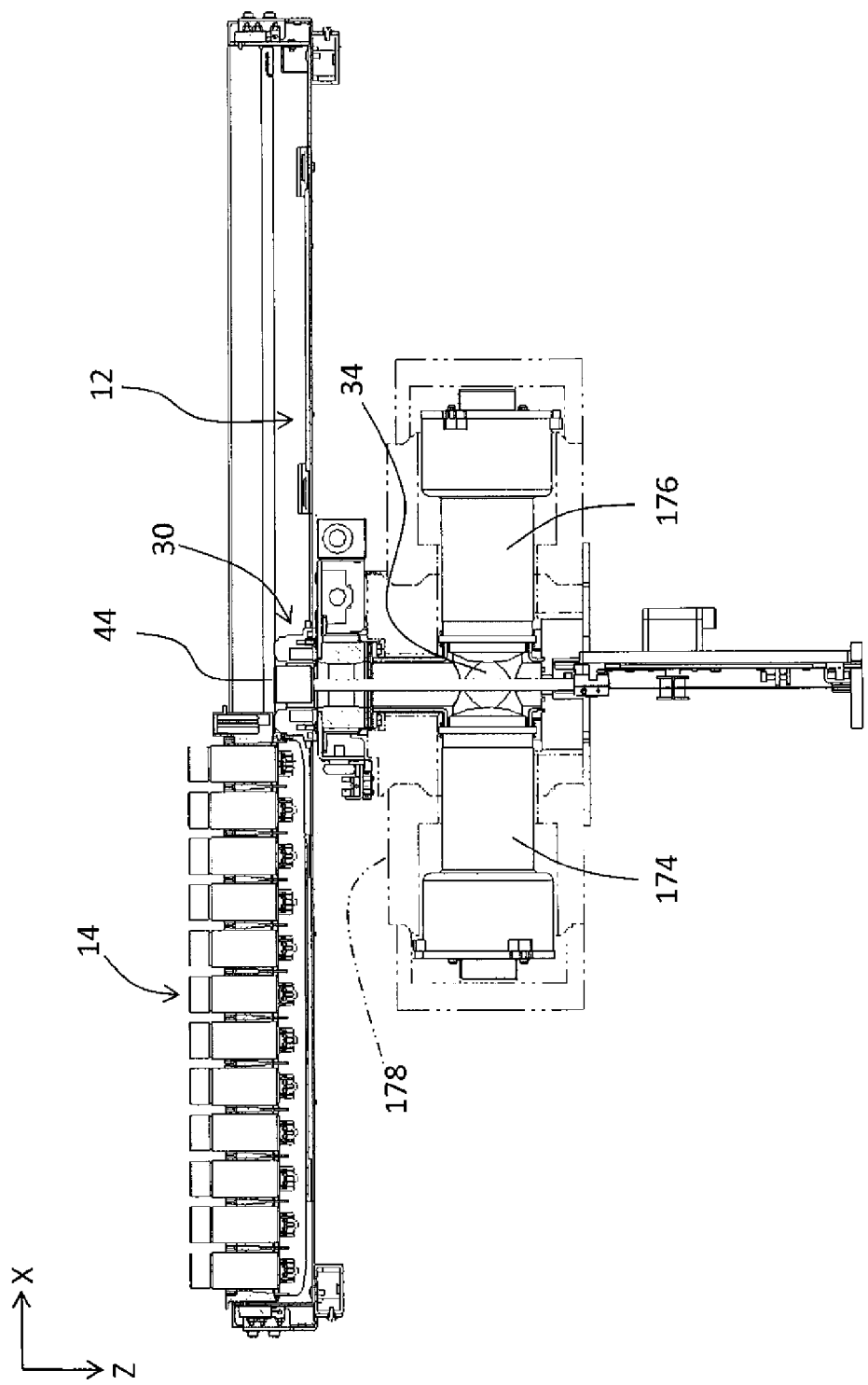
FIG. 28 is an XZ cross sectional diagram showing a head lifted state.

Next, a structure of a lower side of the transport surface will be described. FIG. 28 shows a state where the rack 14 is introduced in the X transport path. In this state, the head 44 is inserted into the opening of the guide block 30. That is, the head 44 is at the uppermost position. The sample measurement chamber 34 is provided immediately below the opening, and a pair of photomultiplier tubes 174 and 176 forming the measurement unit are provided on respective sides of the sample measurement chamber 34. A shielding structure 178 is provided in a manner to wrap the entirety of the sample measurement chamber 34 and the pair of photomultiplier tubes 174 and 176. The shielding structure 178 is formed from lead or the like, and blocks radiation reaching from the outside. However, shielding in the lifting/lowering path is executed by the shutter mechanism to be described later.

Figure 29:
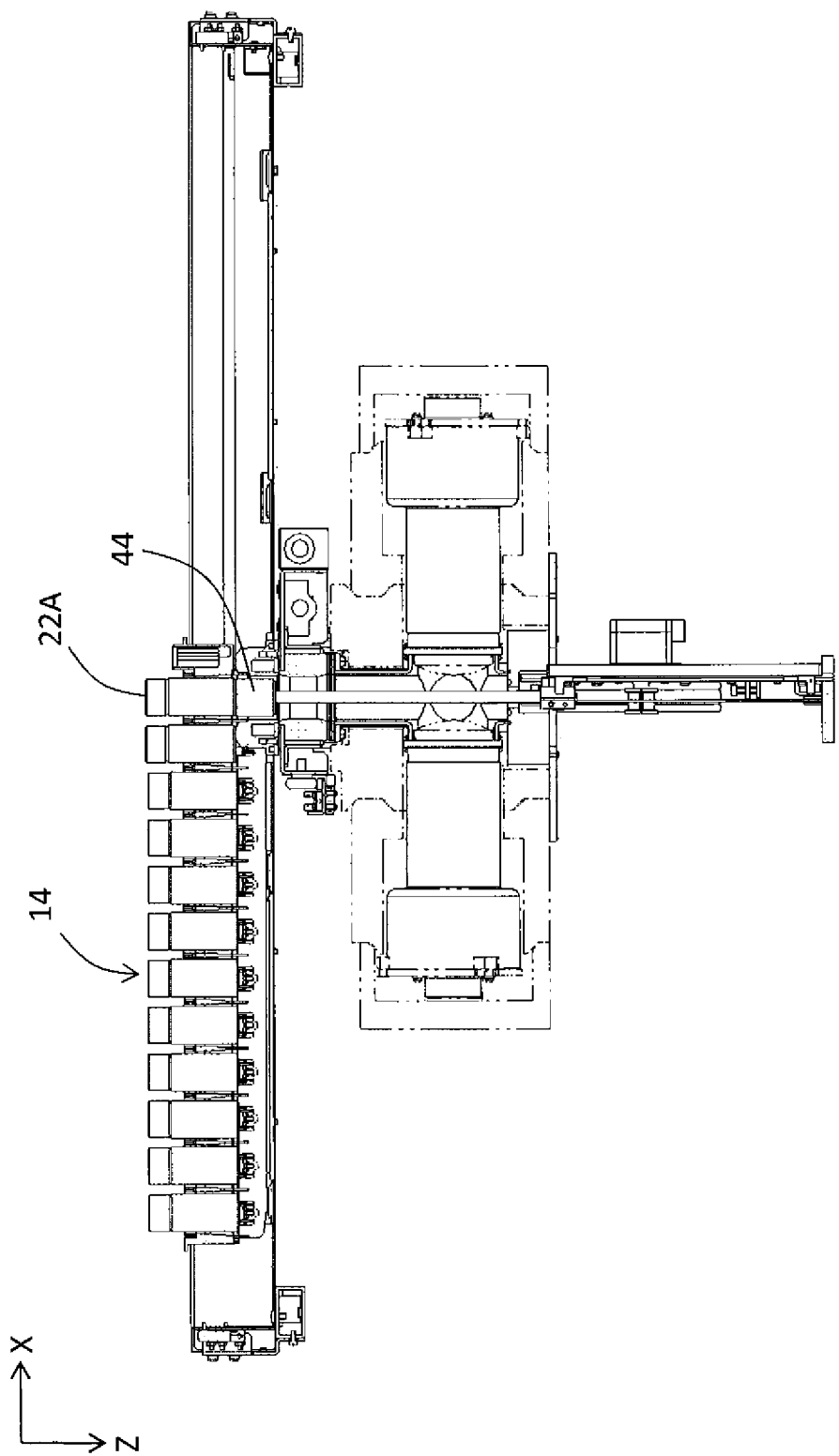
FIG. 29 is an XZ cross sectional diagram showing a handing state of a sample container.

FIG. 29 shows a state where a front-most sample container 36 is moved onto the head 44. In this state, the open/close mechanism described above is in the open state by the function of the guide block.

Figure 30:
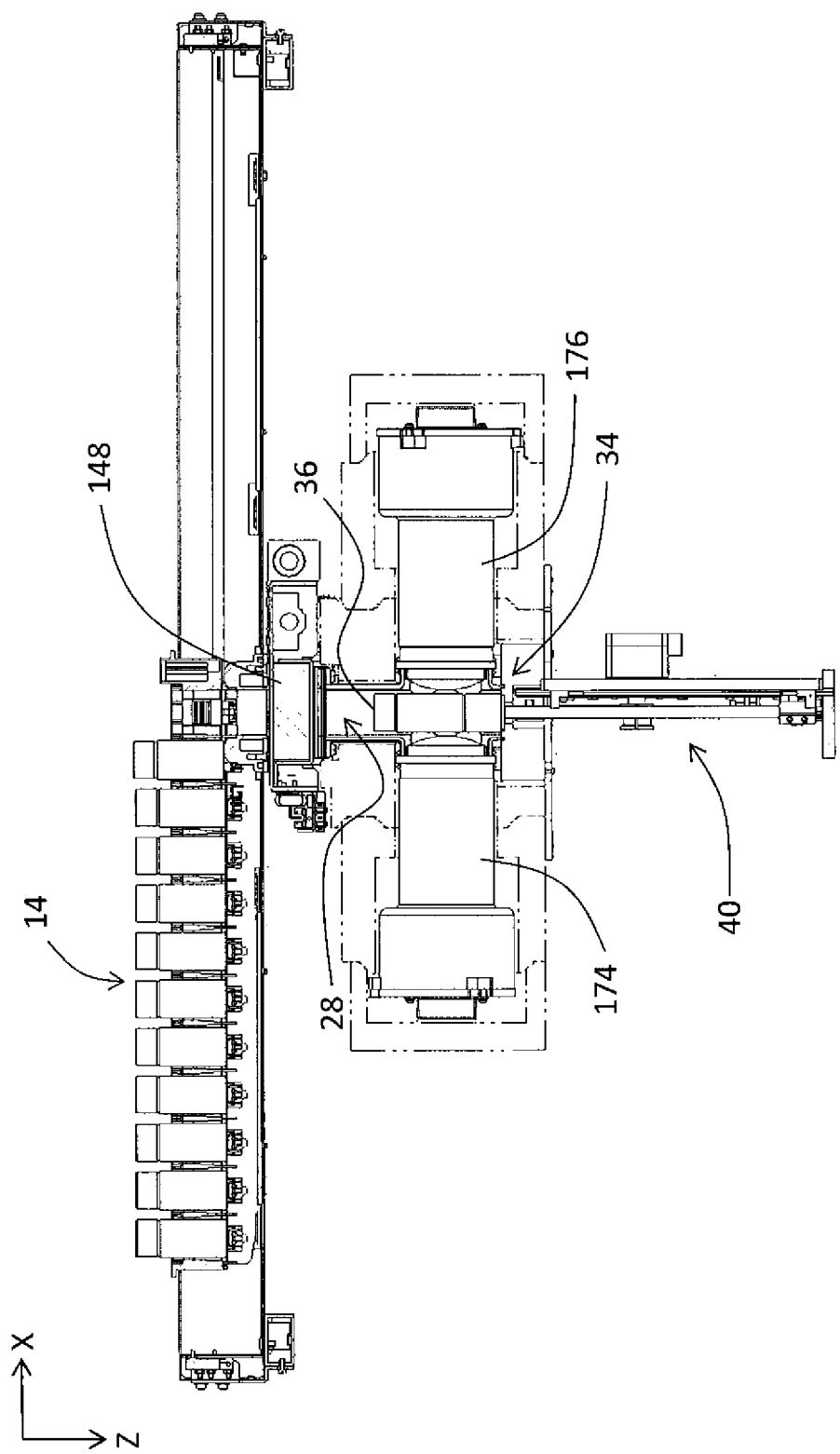
FIG. 30 is an XZ cross sectional diagram showing a sample measurement state.

FIG. 30 shows a sample measurement state. The sample container 36 which is set as a measurement target is placed in the sample measurement chamber 34 by the function of the lifting/lowering mechanism 40. In other words, the sample container 36 is placed between the pair of photomultiplier tubes 174 and 176 in a non-contact state with the photomultiplier tubes. In the sample measurement state, the shutter mechanism is operated across the lifting/lowering path 28. In FIG. 30, the lead block 148 is inserted across the lifting/lowering path 28. Along with the lead block 148, a light-shielding plate to be described later is inserted across the lifting/lowering path 28.

Figure 31:
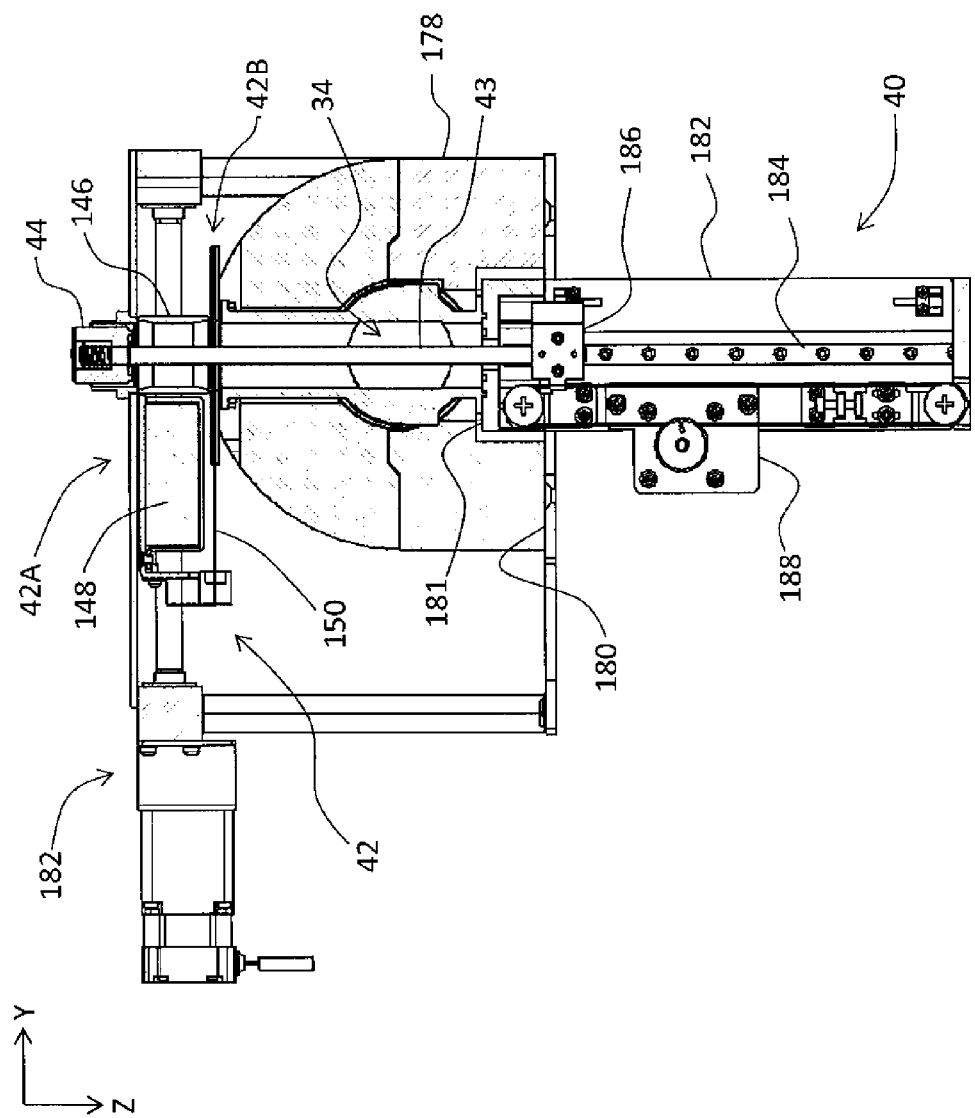
FIG. 31 is a YZ cross sectional diagram showing a head lifted state.

FIG. 31 shows a YZ cross section of the sample measurement device. FIG. 31 shows a non-measurement state. In FIG. 31, the head 44 is at a position of a lifted end. The lifting/lowering mechanism 40 has a vertical plate 182, and a rail 184 is attached on the vertical plate 182. A slide block 186 is provided to be movable in the up-and-down direction with respect to the rail 184. A lower end of the shaft 43 is attached to the slide block 186. The head 44 is attached to an upper end of the shaft 43. A drive force of a motor 188 is transmitted to the slide block 186, which is then driven in the up-and-down direction. With this movement, the shaft 43 and the head 44 also move in the up-and-down direction. The vertical plate 182 is connected to a base frame 181 and a base plate.

A case to be described later is fixed on the base frame 181. The shielding structure 178 is provided on the base plate 180 in a manner to wrap the sample measurement chamber 34 and the case. As described above, the shielding structure 178 is formed from lead or the like.

The shutter mechanism 42 includes the upper shutter mechanism 42A and the lower shutter mechanism 42B. The upper shutter mechanism 42A has the lead block 148 that blocks extrinsic radiation, and the tube guide 146. The lower shutter mechanism 42B has the shielding plate to be described later in detail.

Figure 32:
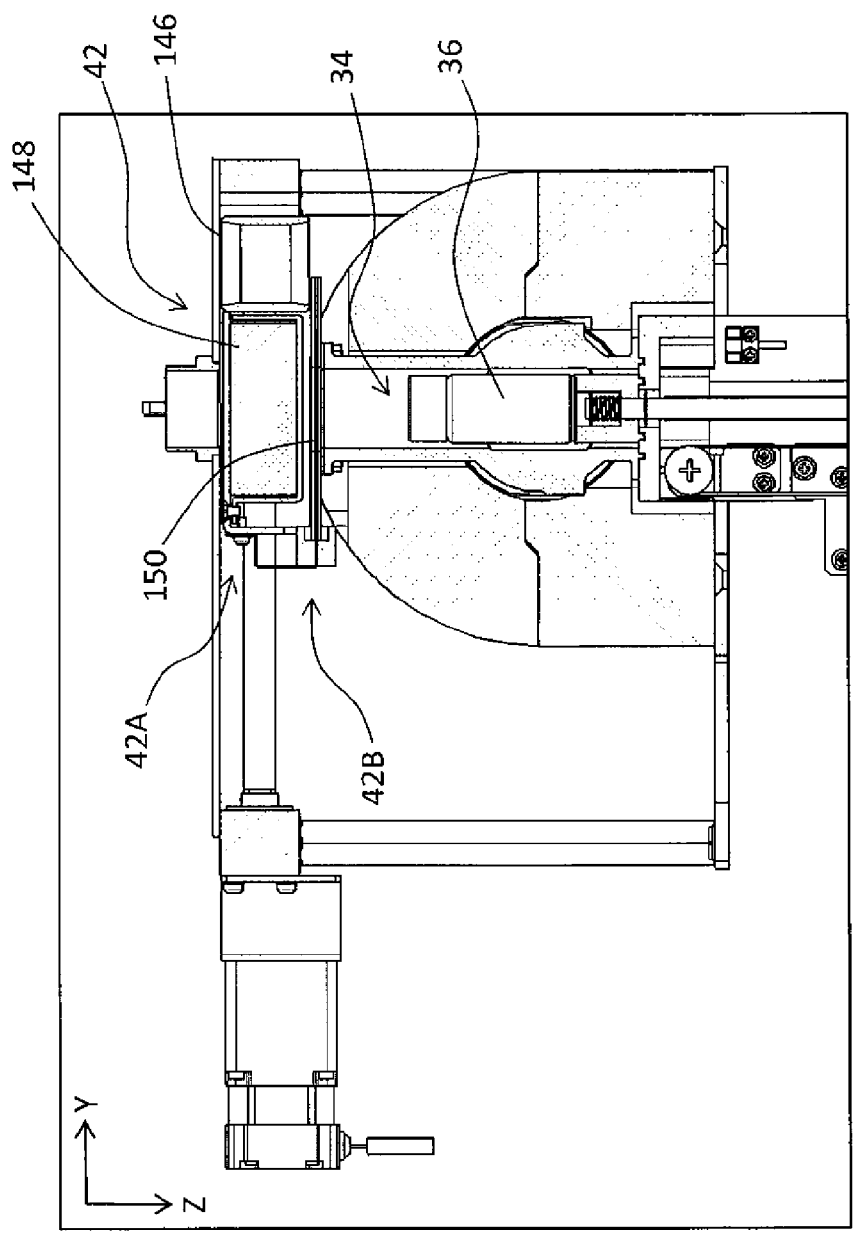
FIG. 32 is a YZ cross sectional diagram showing a shutter operation state.

FIG. 32 shows the YZ cross section of the sample measurement device as an enlarged view. FIG. 32 shows the sample measurement state. The sample container 36 is placed in the sample measurement chamber 34. As described above, the shutter mechanism 42 has the upper shutter mechanism 42A and the lower shutter mechanism 42B. The upper shutter mechanism 42A has the lead block 148 and the tube guide 146. In FIG. 32, the lead block 148 is placed across the lifting/lowering path. In addition, the light-shielding plate 150 is inserted across the lifting/lowering path. In this state, the extrinsic radiation from above is blocked, and, at the same time, the extrinsic light from above is blocked. With this configuration, a sample measurement of high precision can be realized.

Figure 33:
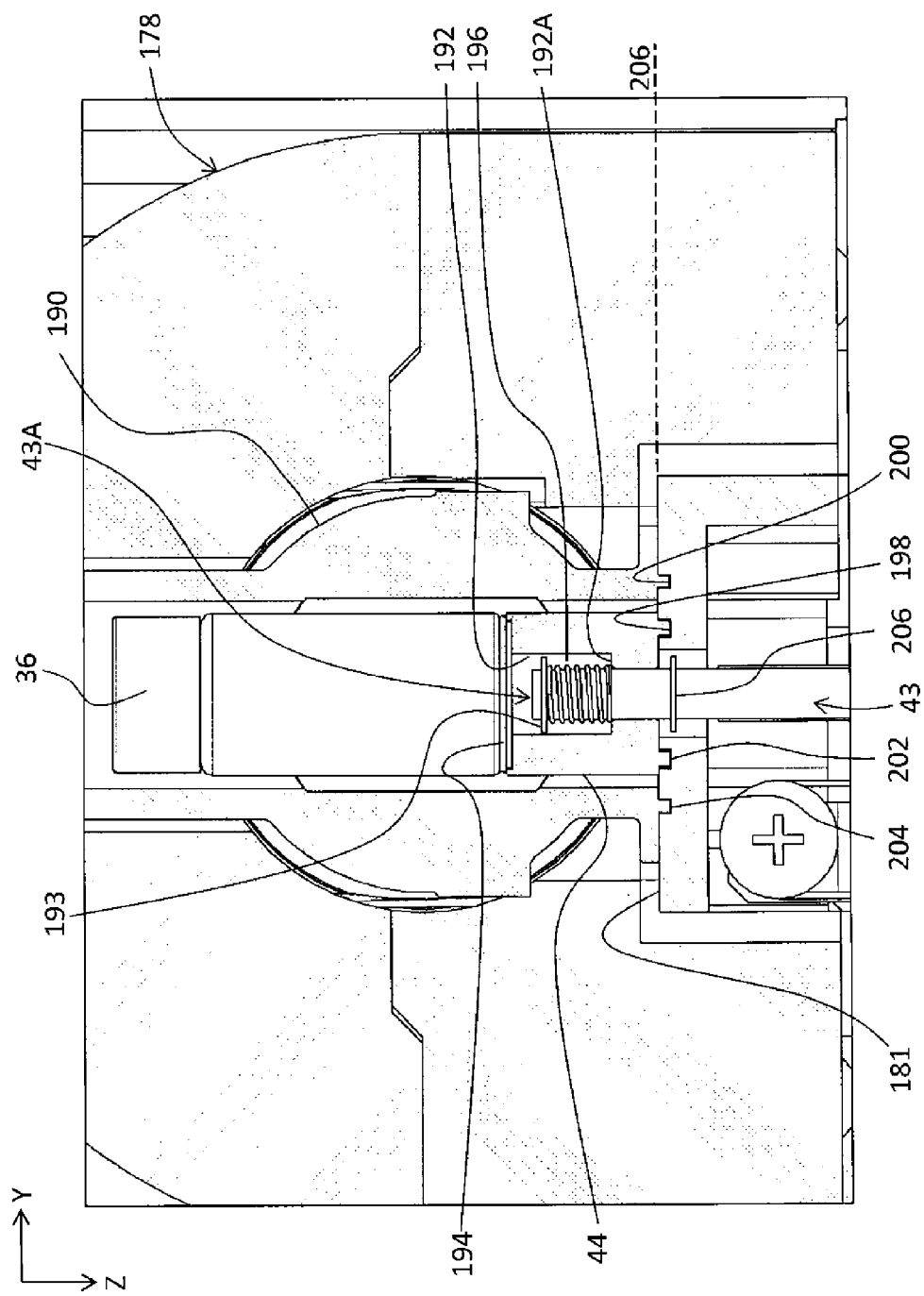
FIG. 33 is an enlarged cross sectional diagram showing a light-shielding structure at a lower part of a sample measurement chamber.

FIG. 33 shows a lower part of the sample measurement chamber as an enlarged view. FIG. 33 shows the sample measurement state. The upper surface of the base frame 181 forms a reference level 206. That is, in the movement control of the sample container 36 in the up-and-down direction, the reference level 206 forms an origin point in the Z direction.

A case 190 having a shape to wrap the sample container 36 is provided on the base frame 181. On the outer side of the case 190, the shielding structure 178 is provided. An opening is formed at the center of the base frame 181, and the shaft 43 passes through the opening. The body of the head 44 is attached to the upper end of the shaft 43.

Specifically, a well 192 is formed in the body of the head 44, and the upper end 43A of the shaft 43 is inserted into the well 192. A ring-shaped stopper 193 is provided on the upper end 43A, and a spring 196 is placed between the stopper 193 and a bottom surface 192A of the well 192.

A top plate 194 is provided in a manner to cover the well 192. The top plate 194 is formed as a layered structure in the present embodiment, and includes at least an elastic sheet at a lower side and a metal reflective layer at an upper side. Alternatively, optical reflection may be produced by painting. The lower elastic member sheet functions as a light-shielding sheet. For example, as shown in FIG. 18 which has already been described, two screw members are used to attach the top plate 194 on the body of the head 44. With such a configuration, a superior light-shielding state is formed.

Because the spring 196 is provided on the upper end 43A of the shaft 43, even if the shaft 43 is lowered slightly excessively, the excess is absorbed by the spring 196. Therefore, the head 44 can be easily lowered to a point where the lower surface of the head 44 closely contacts the upper surface of the base frame 181; that is, the reference surface. In addition, in such a close contact state, as will be described below, a superior light-shielding state can be formed. The stopper 206 is fixedly placed below the head 44 in the shaft 43, and even when the spring 196 is changed from a compressed state to an elongated state, the amount of change is restricted by the stopper 206. In other words, the elongation of the spring 196 is allowed until the stopper 206 contacts the lower surface of the head 44.

Next, the light-shielding structure (inner light-shielding structure) will be described. The light-shielding structure is a structure constructed over the upper surface of the base frame 181 and the lower surface of the head 44.

A first ring groove 198 is formed on the upper surface of the base frame 181 in a manner surrounding the opening through which the shaft 43 passes. In correspondence to this structure, a first ring protrusion 202 is formed on the lower surface of the head 44. In a state where the head 44 is positioned at the lowermost position; that is, the defined position, the first ring protrusion 202 enters the first ring grove 198, and a state is formed in which the protrusion and the groove are fitted. In this case, the shaft 43 is slightly lowered exceeding the lowermost position of the head by a controller (not shown). With this process, an elastic action by the spring 196 is realized. That is, a force pressing the head 44 downward is produced by the spring 196. As a result, a superior close contact state is formed between the first ring groove 198 and the first ring protrusion 202. That is, a superior light-shielding state can be formed. Thus, it becomes possible to reliably block extrinsic light entering the inside of the sample measurement chamber along the outer surface of the shaft 43 and the upper surface of the base frame 181. In addition, with the fitting between the first ring groove 198 and the first ring protrusion 202, a positioning function in the horizontal direction can be obtained for the head 44, with which the sample container 36 can be appropriately positioned in the sample measurement chamber.

In the present embodiment, an outer light-shielding structure is constructed at an outer side of the inner-light shielding structure described above. Specifically, a second ring groove 200 is formed on the upper surface of the base frame 181 in a manner to surround the first ring groove 198. On the other hand, a second ring protrusion 204 is formed on the lower surface of the leg of the case 190 in a manner to surround the first ring protrusion 202. The second ring protrusion 204 enters the inside of the second ring groove 200 in the assembly state, to form a fitted state between the protrusion and the groove. With this configuration, it becomes possible to reliably block the extrinsic light attempting to enter the inside of the sample measurement chamber from the periphery of the base frame 181 along the upper surface of the base frame 181.

The extrinsic light entering the head 44 along the outer surface of the shaft 43 is blocked at the inside of the head 44. That is, the top plate 194 has the light-shielding sheet, which is fixed in a closely contacted manner with respect to the body of the head 44, and the extrinsic light is confined in the head 44 by the light-shielding sheet. In other words, intrusion of the extrinsic light through a gap between the top plate 194 and the body of the head 44 is prevented. In order to achieve sufficient light shielding in the head 44, desirably, a sheet made of a black elastic material is used as the light-shielding sheet. The body of the head 44 is formed from, for example, a hard resin or the like. The base frame 181 is formed from a metal or the like. The case 190 is formed from a metal.

Figure 34:
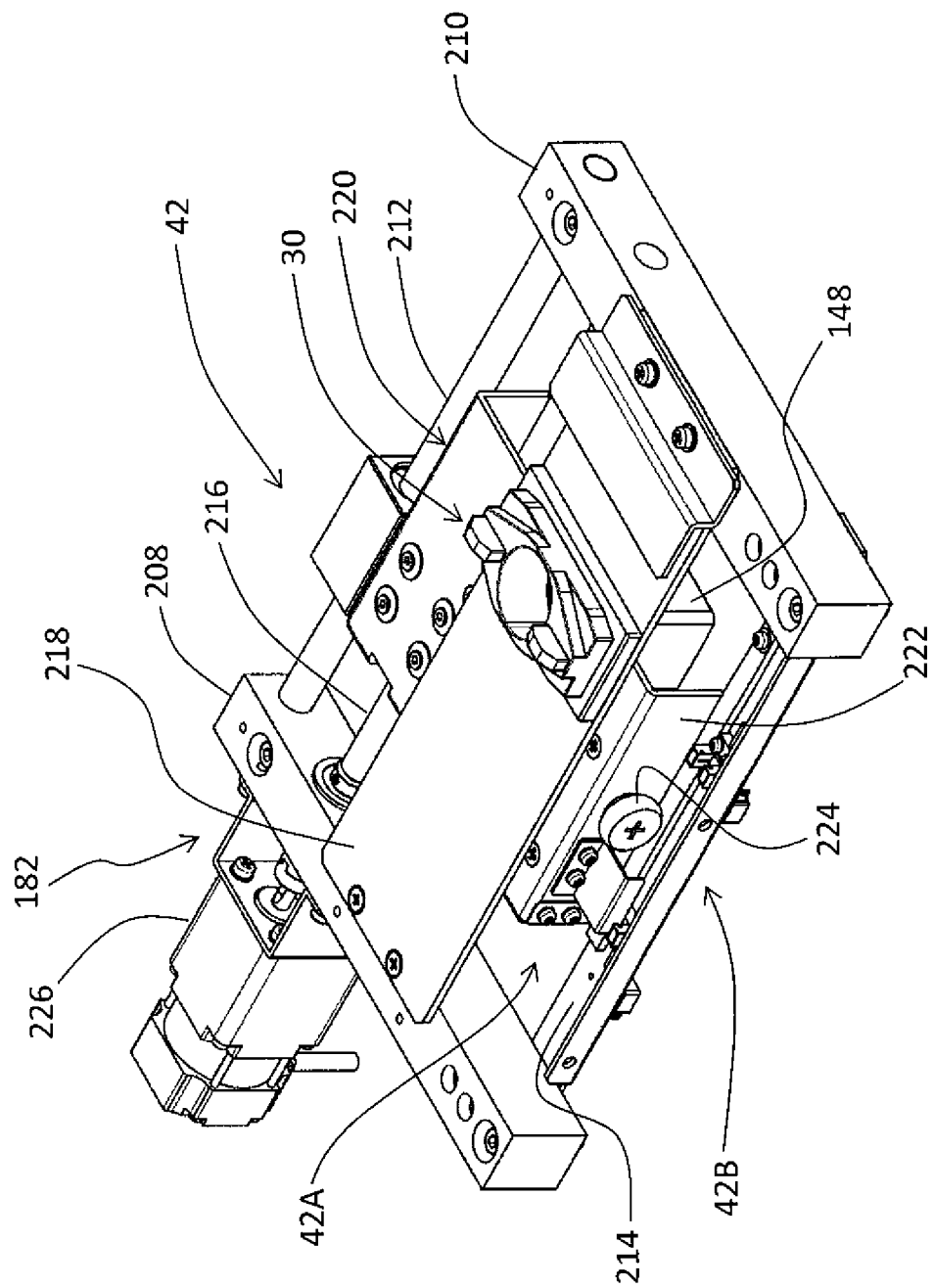
FIG. 34 is a first perspective view of a shutter mechanism.
Figure 35:
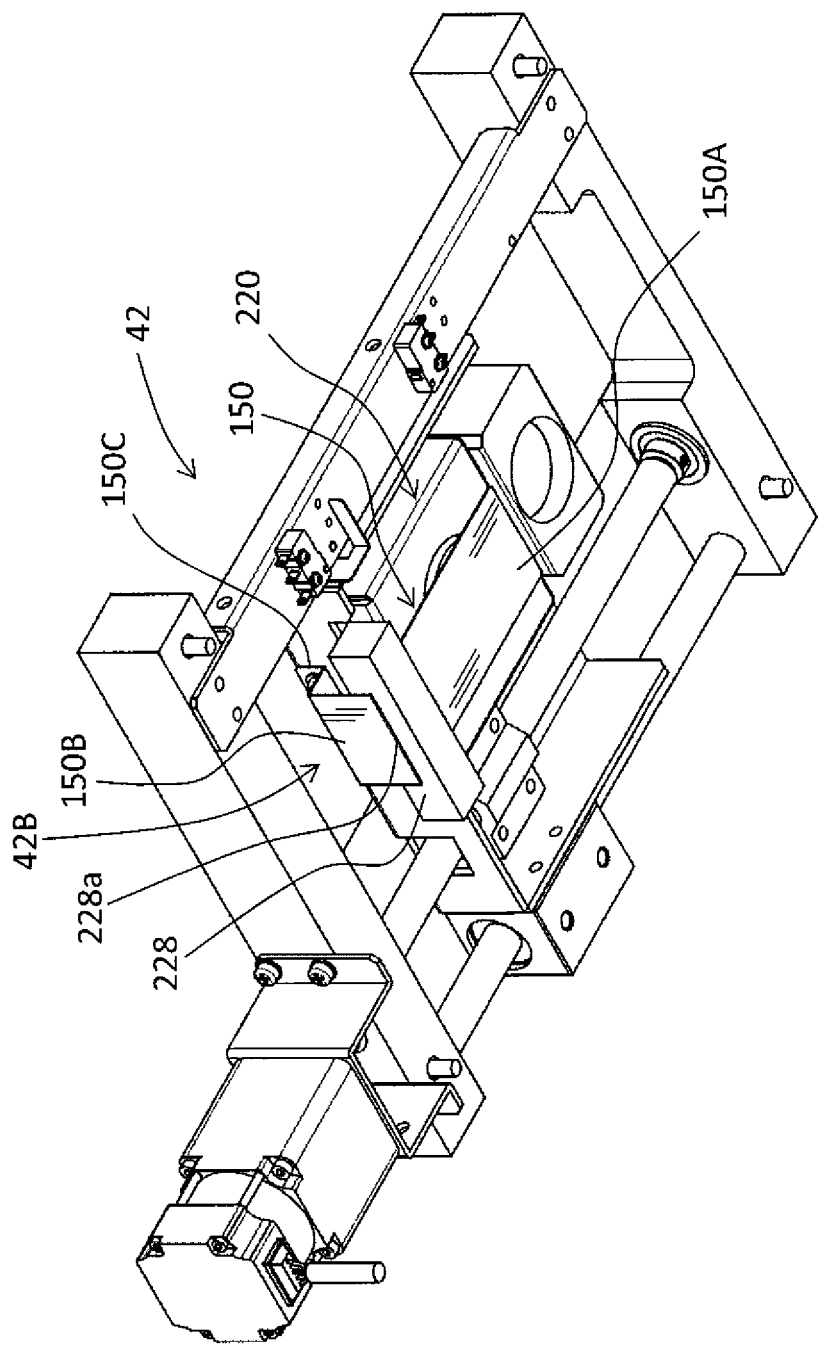
FIG. 35 is a second perspective view of a shutter mechanism.
Figure 36:
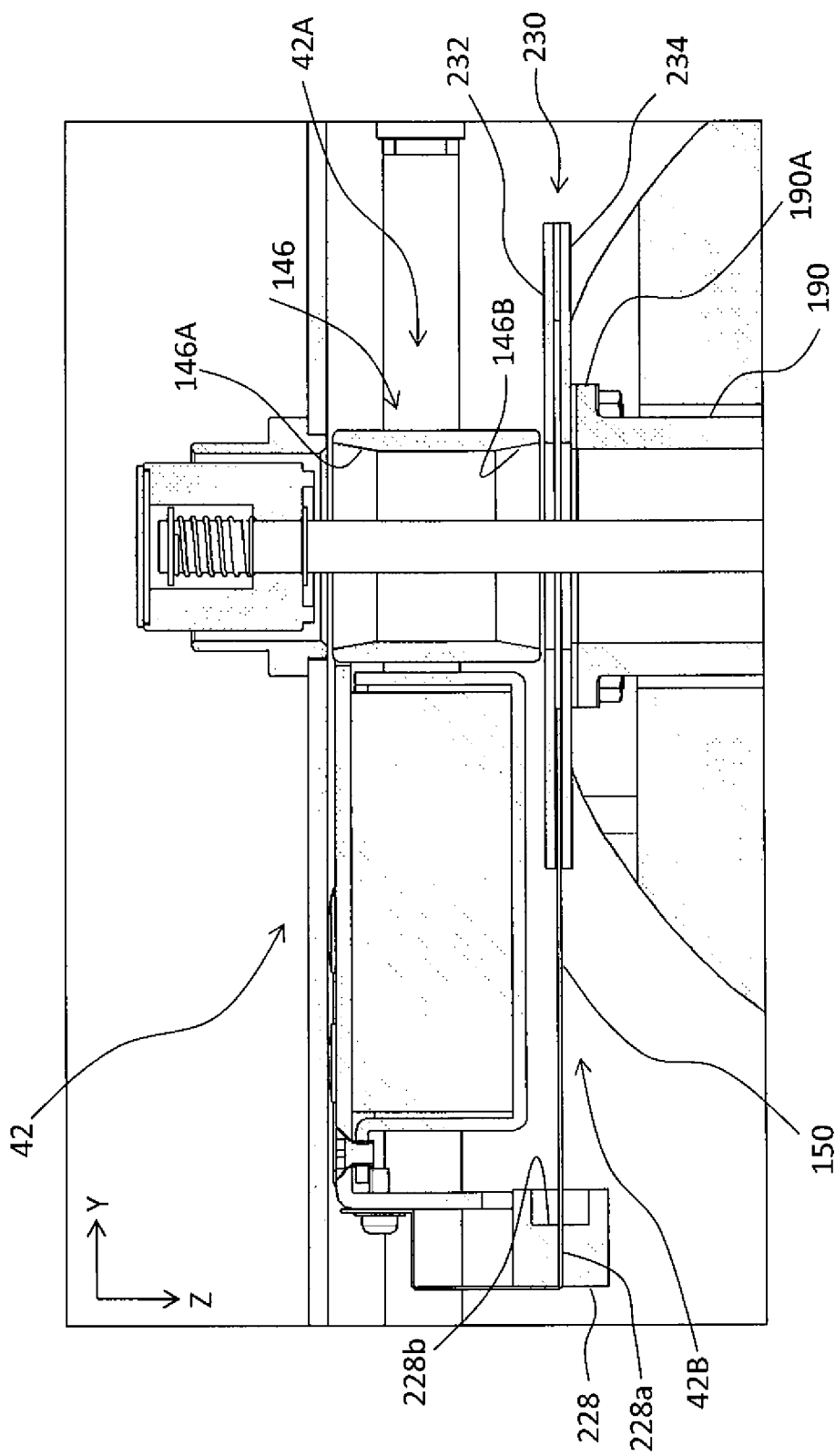
FIG. 36 is a cross sectional diagram of a shutter mechanism.

(F) Light-Shielding Unit (FIGS. 34-36)

FIG. 34 shows a first perspective view of the shutter mechanism 42. Specifically, FIG. 34 shows the shutter mechanism 42 as viewed from diagonally above.

As already described, the shutter mechanism 42 has the upper shutter mechanism 42A and the lower shutter mechanism 42B. The upper and lower shutter mechanisms are attached to a fixed structure. Specifically, fixed blocks 208 and 210 are provided in parallel with each other, and a shaft 212 and a guide member 214 are placed between the fixed blocks. A block is attached in a slidable manner on the shaft 212, and forms a part of a movable member 220. The guide member 214 forms a guide rail, and a roller 224 of the movable member 220 rotationally moves on the guide member.

A block base 218 spreading in the horizontal direction is provided over the fixed block 208 and the fixed block 210. The block base 218 is a member corresponding to the top frame 122 shown in FIG. 13. That is, the guide block 30 is fixed on the block base 218. A motor 226 forms a single drive source in the slide mechanism 182, and a feed screw 216 is driven by the motor 226. In the present embodiment, the feed screw 216 is formed by a trapezoidal screw. A block (not shown) is connected to the trapezoidal screw 216, and, with the rotation of the feed screw 216, the movable member 220 having the block moves in the horizontal direction. The upper shutter mechanism 42A is attached to a movable frame of the movable member 220, and, similarly, the lower shutter mechanism 42B is also attached to a movable frame 222.

FIG. 35 shows a second perspective view of the shutter mechanism 42. Specifically, FIG. 35 shows the shutter mechanism 42 as viewed from diagonally below. The movable member 220 includes the upper shutter mechanism 42A and the lower shutter mechanism 42B. The lower shutter mechanism 42B has the light-shielding plate 150. The light-shielding plate 150 is formed from, for example, a thin metal plate, and examples of the materials forming such a metal plate include zinc, copper, and the like. Preferably, the light-shielding plate 150 is formed from a metal having a light-shielding function and also a function to block a braking radiation. A braking radiation is a radiation secondarily produced when the extrinsic radiation is blocked by the lead block.

The light-shielding plate 150 has a body 150A forming a horizontal portion, and a bent portion 150B continuous from the body 150A, and the bent portion 150B forms a vertical portion. Further, the bent portion 150B is connected to an attachment portion 150C, and the attachment portion 150C is fixed on the movable frame described above. On a base end side of the body 150A of the light-shielding plate 150, an elastic member block 228 is provided. Specifically, the elastic member block 228 has a slit 228A formed therethrough in the horizontal direction, and a part of the body 150A; in particular, a part of the base end, is inserted into the slit 228A. The slit 228A and the body 150A are not fixed with respect to each other, and a relative horizontal movement is allowed. The elastic member block 228 may be fixed on the movable frame or simply attached to the body 150A. The elastic member block 228 is formed from, for example, a rubber member or the like. In FIG. 35, a slit structure (fixed structure) which receives the body 150A in the light-shielding plate 150 is omitted in the drawing.

FIG. 36 shows a cross sectional diagram of the shutter mechanism 42. As described above, the upper shutter mechanism 42A has the lead block and the tube guide 146 arranged in the horizontal direction. When the lead block is at the retracted position, the tube guide 146 is positioned on the lifting/lowering path, and the centering function (alignment function) with respect to the sample container or the like is realized.

Specifically, on the inner surface of the tube guide 146, a tapered surface 146A is employed at the upper end portion, and a tapered surface 146B is employed at the lower end portion. With these inclined surfaces, when the sample container moves from the upper part toward the lower part or when the sample container moves from the lower part toward the upper part, even if there is a position deviation in the horizontal direction, the sample container can be positioned at an appropriate position in the horizontal direction by the function of the inclined surfaces. Alternatively, the alignment function with respect to the head may be realized.

Next, the lower shutter mechanism 42B will be described. FIG. 36 shows a slit structure 230. The slit structure 230 forms a part of the lower shutter mechanism 42B, and is a fixed structure. The slit structure 230 can be roughly divided into an upper plate 232 and a lower plate 234, and a slit is formed between the plates. The periphery of the slit is sealed except for the entrance which accepts the light-shielding plate 150. That is, entrance of light into the slit from the outside is blocked.

The light-shielding plate 150 is in the retracted position in FIG. 36, and, in this case, only the tip of the light-shielding plate 150 enters the slit structure 230. The light-shielding plate 150 is at a position completely deviated from the lifting/lowering path.

The elastic member block 228 is attached to the base end side of the light-shielding plate 150. The elastic member block 228 has the horizontal slit 228a, and the light-shielding plate 150 penetrates therethrough. When the shutter mechanism 42 executes the shutter operation, the movable portion in the upper shutter mechanism 42A and the movable portion in the lower shutter mechanism 42B move from the retracted position toward a front position. With this configuration, the lead block is inserted at the upper side on the lifting/lowering path, and the light-shielding plate 150 is inserted to the lower side. With such a double shutter state, the extrinsic radiation is blocked, and, at the same time, the extrinsic light is blocked. The slit structure 230 is fixed at the upper end of the case 190 described above.

When the movable portion in the lower shutter mechanism 42B reaches the forward position, the end of the slit structure 230 is inserted in a recess 228B serving as a depression formed in the elastic member block 228, and an end surface of the end strongly contacts a back surface of the recess 228B. In other words, the slit structure and the recess are strongly and closely contacted with each other. With this process, the intrusion of the extrinsic light into the inside of the slit through the slit entrance of the slit structure 230 can be reliably blocked. On the attachment end side of the light-shielding plate 150, a certain deflection portion such as the vertical portion is present, and, when the light-shielding plate 150 is pressed to the front end, the reaction thereof can be absorbed by the base end side of the light-shielding plate 150.

According to the shutter mechanism of the present embodiment, shielding of the radiation and shielding of the light can be simultaneously executed with a single drive source and a single slide mechanism, and, thus, it is possible to simplify the mechanism, and at the same time, the control. In addition, because the light-shielding plate is formed from a member having a function to block or attenuate the braking radiation, an advantage can be obtained in that, even if the braking radiation is produced at the lead block, reaching of the radiation to the sample measurement chamber can be effectively reduced.

Further, because the elastic block is provided at a root side of the light-shielding plate and the intrusion of the extrinsic light into the inside of the slit structure is blocked by close contact of the slit structure to which the light-shielding plate is inserted and the elastic member block, an advantage can be obtained in that the extrinsic light entering from the periphery can be effectively blocked in addition to the extrinsic light coming in from above and through the lifting/lowering path. In the present embodiment, because the sample measurement chamber is provided on a lower side of the transport table; that is, because there is no shaft in the lifting/lowering path when the shutter mechanism is operated, an advantage can also be obtained in that the structure of the shutter mechanism can be simplified.

(G) Alternative Configuration of Adapter (FIGS. 37-40)
Next, an alternative configuration of the adapter will be described with reference to FIGS. 37-40.

Figure 37:
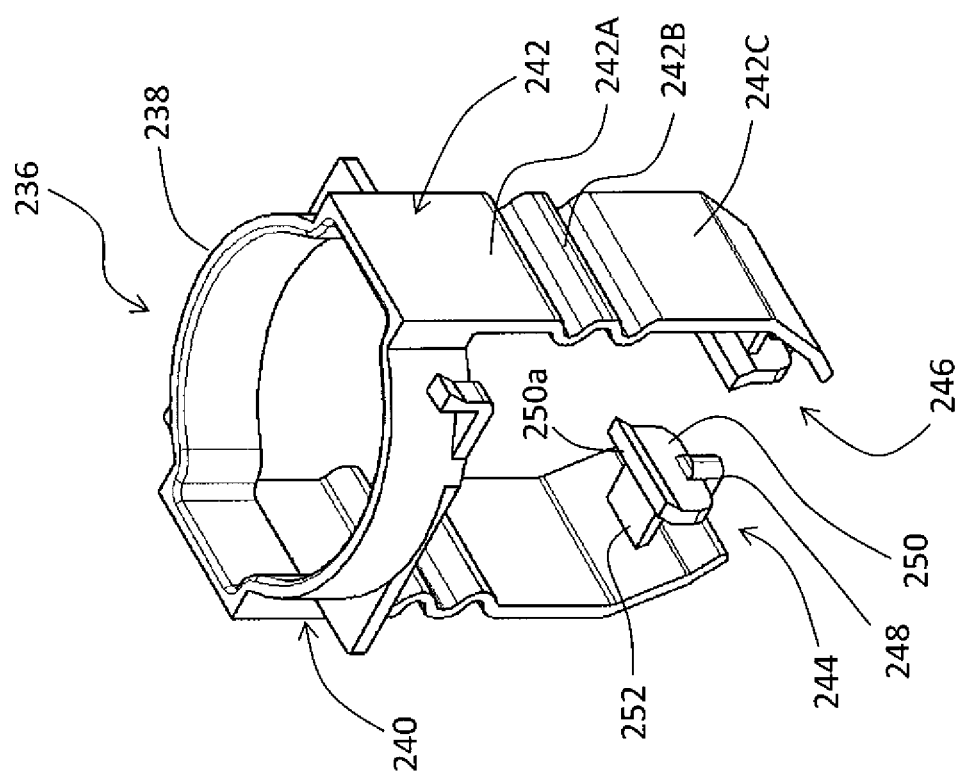
FIG. 37 is a first perspective view showing another adapter.

FIG. 37 shows a first perspective view of an adapter 236 according to a second preferred embodiment of the present invention. The adapter 236 has an annular frame 238 and a pair of arms 240 and 242 connected thereto. The arm 240 and the arm 242 have shapes symmetric from each other. The arm 242 will be described as a representative of the two arms. The arm 242 has an upper portion 242A, a wave-shaped portion 242B, and a lower portion 242C. A lower end structure 246 is formed in the lower portion 242C. Similarly, the arm 240 has a lower end structure 244.

The lower end structure 244 and the lower end structure 246 has a structure symmetric from each other. The lower end structure 244 has a rib 248 protruding in the horizontal direction and a support plate 250 fixed thereto. An upper end 250a of the support plate 250 has an inclined portion inclined in the inner side. A reinforcement plate 252 extending from the arm body is connected to an intermediate position of the support plate 250.

Figure 38:
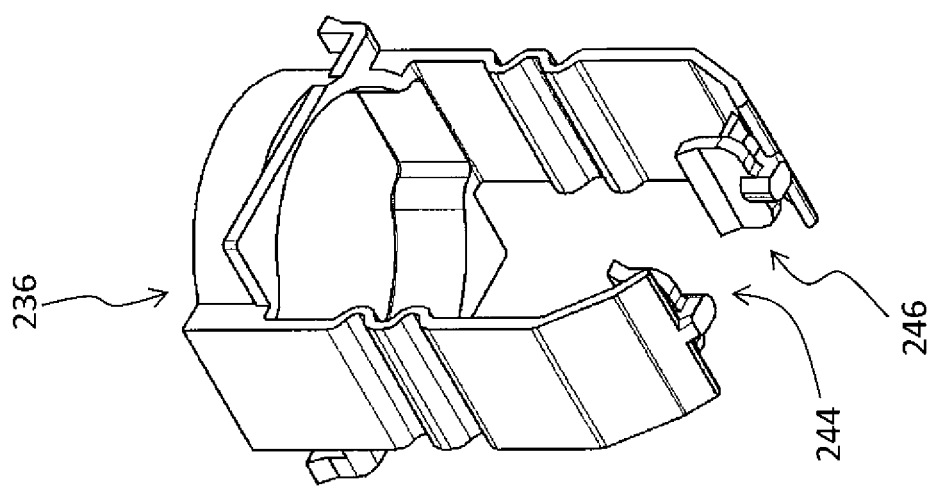
FIG. 38 is a second perspective view showing another adapter.

FIG. 38 shows a second perspective view of the adapter 236. As described above, in the arms, the lower end structures 244 and 246 are formed.

Figure 39:
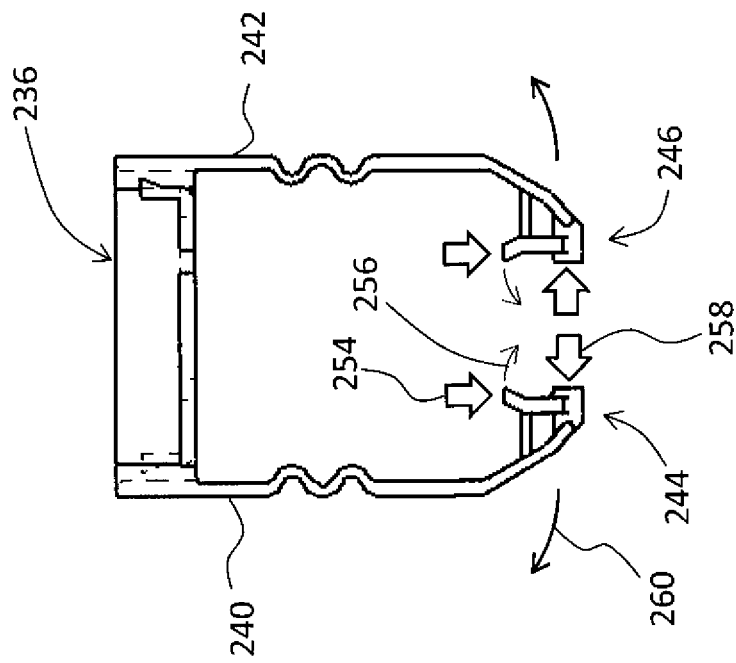
FIG. 39 is a schematic view explaining an operation of another adapter.

Functions of the lower end structures 244 and 246 will now be described with reference to FIG. 39. When an opening force 258 is applied to the outer side in the horizontal direction by the contact with the guide block, the lower end structures 244 and 246 move toward the outer side in the horizontal direction. This movement is shown by a reference numeral 260. On the other hand, when an excessive pressing force 254 is applied from above and through the sample container in a state where the two arms 240 and 242 are in the closed state, the upper end portion of the support plate is deformed in a manner to fall toward the inside as shown by a reference numeral 256. With such a deformation, all or a primary portion of the pressing force 254 from above is absorbed. In other words, because the pressing force is concentrated in the deformation portions of the lower end structures 244 and 246, no opening movement of the two arms 240 and 242 as described above is caused.

In the first preferred embodiment of the present invention described above with reference to FIG. 12 or the like, the stopper connected to the deformation portion is used. In contrast, in the present embodiment, erroneous operation by the pressing force from above is prevented using the deformation portion which moves to fall toward the inside. In both preferred embodiments, deformation is effectively used.

Figure 40:
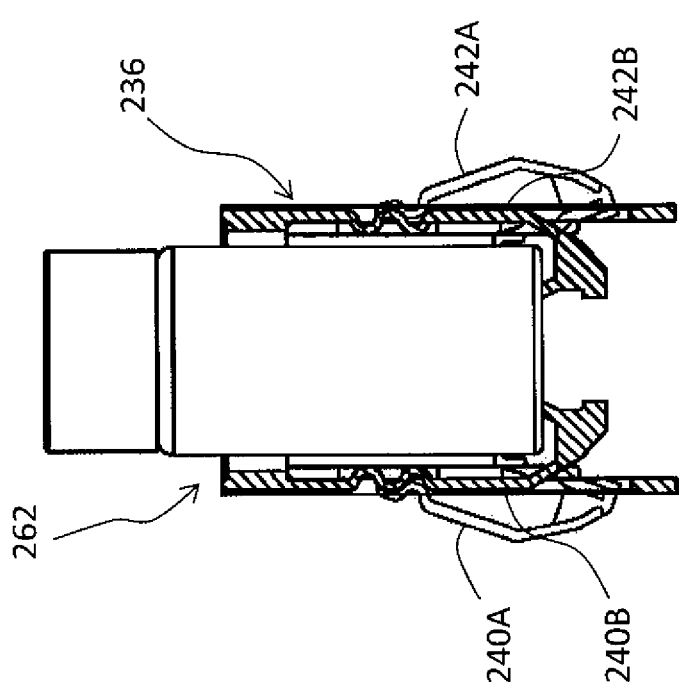
FIG. 40 is a cross sectional diagram for explaining an operation of another adapter.

FIG. 40 shows a cross sectional diagram of the rack. The adapter 236 described above is attached on the rack body 262. Reference numerals 240A and 242A show a state where the arms are opened, and reference numerals 240B and 242B show a state where the arms are closed. As described above, even when the pressing force is applied from above in the closed state, the pressing force is absorbed by the elastic deformation of a part of the structure, and the opening movement of the pair of arms is effectively prevented. In the case where the adapter according to the second preferred embodiment of the present invention is used also, the guide block shown in FIG. 18 or the like is used.

The invention claimed is:
1. A sample measurement device, comprising:
a rack that has a longitudinal direction and a short-side direction orthogonal to the longitudinal direction, that has a pair of legs distanced from each other in the short-side direction, and that has a sample storage unit having an open/close mechanism including a pair of contact members:
a rack-transporting mechanism that transports the rack on a transport surface;
a guide block provided on the transport surface that enters a lower part of the rack during transport of the rack and that has a lower layer that enters a region between the pair of the legs for centering the rack in the short-side direction and an upper layer that is a layer above the lower layer and that enters a region between the pair of the contact members to set the open/close mechanism to an open state; and
a lifting/lowering mechanism that transports a sample container between the sample storage unit and a sample measurement chamber provided below the transport surface in an open state of the open/close mechanism;
wherein:
the sample measurement device measures a radioactive substance in a sample housed in the sample container when the sample container is set in the sample measurement chamber;
the upper layer has:
a front-side form that contacts the pair of contact members of the open/close mechanism during relative movement of the rack with respect to the guide block, to transition the open/close mechanism from a closed state to an open state; and
a rear-side form that contacts the pair of contact members of the open/close mechanism during the relative movement, to recover the open/close mechanism from the open state to the closed state;

holding of the sample container is executed in the closed state; and holding of the sample container is released in the open state.

2. The sample measurement device according to claim 1, wherein
the front-side form has a pair of front-side included surfaces that apply a press-spreading force on the open/close mechanism.

3. The sample measurement device according to claim 2, wherein
the rear-side form has a pair of rear-side inclined surfaces that allow a recovery movement of the open/close mechanism.

4. The sample measurement device according to claim 1, wherein
the upper layer has an intermediate form provided between the front-side form and the rear-side form that maintains the open state of the open/close mechanism, and
the intermediate form has an opening that forms an upper end portion of a lifting/lowering path of the sample container.

5. The sample measurement device according to claim 4, wherein
the guide block has:
a front-side protrusion provided at a front side of the opening that temporarily supports a lower surface of the sample container from below, after holding of the sample container by the open/close mechanism disappears; and
a rear-side protrusion provided at a rear side of the opening that temporarily supports the lower surface of the sample container from below, until the holding of the sample container by the open/close mechanism is resumed.

6. The sample measurement device according to claim 5, wherein
the lifting/lowering mechanism has a head that has a placement surface on which the sample container is placed, and
in a state where the head is inserted into the opening, the placement surface is positioned at substantially the same height as an upper surface level of the front-side protrusion and the rear-side protrusion.

7. The sample measurement device according to claim 1, wherein
the lower layer has a front end portion, an intermediate portion, and a rear end portion arranged along the longitudinal direction,
the front end portion has a tapered from and
a width of the intermediate portion in the short-side direction is substantially equal to a gap between the pair of the legs.

8. The sample measurement device according to claim 1, wherein
the rack has a plurality of sample storage units arranged along the longitudinal direction,
each sample storage unit respectively has the open/close mechanism, and
the guide block causes the plurality of open/close mechanisms to be sequentially opened and closed while passing a region between the pair of the legs during a transport process of the rack in the longitudinal direction.

9. The sample measurement device to according to claim 1, further comprising:
a pressing unit provided on one side of the guide block, having a pressing mechanism that applies a pressing force on an outer surface of one leg in the rack to cause an inner surface of the one leg to closely contact the guide block and form a state of an appropriate position and an appropriate orientation of the rack.

10. The sample measurement device according to claim 9, wherein
the pressing unit has:
a first contact member that applies a first pressing force on the outer surface of the one leg; and
a second contact member provided at a position distanced from the first contact member that applies a second pressing force on the outer surface of the one leg.

11. The sample measurement device according to claim 10, wherein
the first contact member is a first roller, and
the second contact member is a second roller.

12. The sample measurement device according to claim 1, wherein
in the process of entry of the guide block of the pair of the legs, inclined surfaces of the lower layer centers the rack in the short-side direction and inclined surfaces of the upper layer sets the open/close mechanism to an open state.

13. A sample transport device, comprising:
a rack that has a longitudinal direction and a short-side direction at an angle to the longitudinal direction, that has a pair of legs distanced from each other in the short-side direction, and that has a sample storage unit having an open/close mechanism including a pair of contact members:
a rack-transporting mechanism that transports the rack on a transport surface;
a guide block provided on the transport surface that enters a lower part of the rack during transport of the rack and that has a lower layer that enters a region between the pair of the legs for centering the rack in the short-side direction, and an upper layer that is a layer above the lower layer and that enters a region between the pair of the contact members to set the open/close mechanism to an open state; and
a lifting/lowering mechanism that transports a sample container between the sample storage unit and a sample measurement chamber provided below the transport surface in an open state of the open/close mechanism;
wherein:
the upper layer has:
a front-side form that contacts the pair of contact members of the open/close mechanism during relative movement of the rack with respect to the guide block, to transition the open/close mechanism from a closed state to an open state; and
a rear-side form that contacts the pair of contact members of the open/close mechanism during the relative movement, to recover the open/close mechanism from the open state to the closed state;
holding of the sample container is executed in the closed state; and
holding of the sample container is released in the open state.

14. A sample transport device, comprising:
a rack that has a longitudinal direction and a short-side direction at an angle to the longitudinal direction, that has a pair of legs distanced from each other in the short-side direction, and that has a sample storage unit having an open/close mechanism including a pair of contact members:

a rack-transporting mechanism that transports the rack on a transport surface;

a guide block provided on the transport surface that enters a lower part of the rack during transport of the rack and that has inclined surfaces on a lower layer that enters a region between the pair of the legs for centering the rack in the short-side direction, and an upper layer that is a layer above the lower layer and that enters a region between the pair of the contact members to set the open/close mechanism to an open state; and a lifting/lowering mechanism that transports a sample container between the sample storage unit and a sample measurement chamber provided below the transport surface in an open state of the open/close mechanism;

wherein:

the upper layer has:

front-side inclined surfaces that contact the pair of contact members of the open/close mechanism during relative movement of the rack with respect to the guide block, to transition the open/close mechanism from a closed state to an open state; and rear-side inclined surfaces that contact the pair of contact members of the open/close mechanism during the relative movement, to recover the open/close mechanism from the open state to the closed state;

holding of the sample container is executed in the closed state; and holding of the sample container is released in the open state.

* * * * *